(12) United States Patent
Shelton

(10) Patent No.: US 12,369,979 B2
(45) Date of Patent: Jul. 29, 2025

(54) SUCTION AND IRRIGATION CONTROL SYSTEM AND METHOD

(71) Applicant: GYRUS ACMI, INC., Southborough, MA (US)

(72) Inventor: Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 258 days.

(21) Appl. No.: 16/803,649

(22) Filed: Feb. 27, 2020

(65) Prior Publication Data
US 2020/0187761 A1   Jun. 18, 2020
US 2020/0405130 A9   Dec. 31, 2020

Related U.S. Application Data

(63) Continuation-in-part of application No. PCT/US2019/017391, filed on Feb. 9, 2019.
(Continued)

(51) Int. Cl.
*A61B 1/015* (2006.01)
*A61B 1/00* (2006.01)
(Continued)

(52) U.S. Cl.
CPC .......... *A61B 18/26* (2013.01); *A61B 1/00006* (2013.01); *A61B 1/00055* (2013.01);
(Continued)

(58) Field of Classification Search
CPC ............ A61B 1/00006; A61B 1/00045; A61B 1/00055; A61B 1/015; A61B 1/018;
(Continued)

(56) References Cited

U.S. PATENT DOCUMENTS 4,971,034 A   11/1990   Doi et al.
5,785,702 A   7/1998   Murphy-Chutorian et al.
(Continued)

FOREIGN PATENT DOCUMENTS

AU   2019216954 B2   2/2024
AU   2019217992 B2   9/2024
(Continued)

OTHER PUBLICATIONS

"International Application Serial No. PCT/US2021/019568, International Search Report mailed May 14, 2021", 4 pgs.
(Continued)

*Primary Examiner* — Philip R Wiest
*Assistant Examiner* — Linnae E. Raymond
(74) *Attorney, Agent, or Firm* — Schwegman Lundberg Woessner, P.A.

(57) ABSTRACT

Systems and methods of in situ pressure control at an anatomical environment during a procedure are disclosed. An exemplary irrigation and suction system comprises a user input configured to receive from a user a desired pressure to be applied to the anatomical environment, or a desired flow condition corresponding to the desired pressure. The system comprises a pressure sensor to sense a pressure at or near the anatomical environment, and a control module to adjust one or more of an irrigation flow rate or a suction flow rate of at least one working channel of a medical device to maintain the pressure of the anatomical environment at substantially a level of the desired pressure, or to maintain the desired flow condition in the working channel during the procedure.

20 Claims, 8 Drawing Sheets

Related U.S. Application Data

(60) Provisional application No. 62/628,513, filed on Feb. 9, 2018.

(51) Int. Cl.
　　*A61B 1/018*　　(2006.01)
　　*A61B 1/06*　　(2006.01)
　　*A61B 1/12*　　(2006.01)
　　*A61B 1/307*　　(2006.01)
　　*A61B 1/31*　　(2006.01)
　　*A61B 17/3207*　　(2006.01)
　　*A61B 18/24*　　(2006.01)
　　*A61B 18/26*　　(2006.01)
　　*A61M 1/00*　　(2006.01)
　　*H01S 3/067*　　(2006.01)
　　*A61B 1/05*　　(2006.01)
　　*A61B 18/00*　　(2006.01)
　　*H01S 3/16*　　(2006.01)

(52) U.S. Cl.
　　CPC .......... *A61B 1/00087* (2013.01); *A61B 1/015* (2013.01); *A61B 1/018* (2013.01); *A61B 1/06* (2013.01); *A61B 1/126* (2013.01); *A61B 1/307* (2013.01); *A61B 1/31* (2013.01); *A61B 18/24* (2013.01); *A61M 1/74* (2021.05); *A61M 1/77* (2021.05); *H01S 3/06716* (2013.01); *A61B 1/00045* (2013.01); *A61B 1/00105* (2013.01); *A61B 1/05* (2013.01); *A61B 17/320783* (2013.01); *A61B 2018/00482* (2013.01); *A61B 2018/00505* (2013.01); *A61B 2018/00511* (2013.01); *A61B 2018/00559* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00773* (2013.01); *A61B 2018/00982* (2013.01); *A61B 2217/005* (2013.01); *A61B 2217/007* (2013.01); *A61B 2562/0247* (2013.01); *A61M 2205/3334* (2013.01); *A61M 2205/3344* (2013.01); *H01S 3/1616* (2013.01)

(58) Field of Classification Search
　　CPC .......... A61B 1/307; A61B 2017/00022; A61B 2018/00505; A61B 2018/00482; A61B 2018/00642; A61B 2018/00696; A61B 2090/064; A61B 2217/007; A61B 2217/005; A61B 2562/0247; A61B 18/26; A61B 18/22; A61B 18/24; A61B 1/00087; A61B 1/06; A61B 1/126; A61B 1/31; A61B 1/00105; A61B 1/05; A61B 17/320783; A61B 17/32002; A61B 2018/00511; A61B 2018/00559; A61B 2018/00672; A61B 2018/00678; A61B 2018/00702; A61B 2018/00773; A61B 2018/00982; A61B 2018/2253; A61B 2217/00022; A61B 90/37; A61B 17/320016; A61M 1/73; A61M 1/74; A61M 1/75; A61M 1/77; A61M 1/772; A61M 2205/3344; A61M 2205/3334; A61M 1/7173; A61M 1/71; A61M 1/774; A61M 3/022; A61M 3/0216; H01S 3/06716; H01S 3/1616; H01S 3/161
　　See application file for complete search history.

(56) References Cited

U.S. PATENT DOCUMENTS

| | | |
|---|---|---|
| 5,931,834 A | 8/1999 | Murphy-Chutorian et al. |
| 6,156,049 A | 12/2000 | Lovato et al. |
| 6,527,716 B1 | 3/2003 | Eppstein |
| 8,109,872 B2 | 2/2012 | Kennedy, II et al. |
| 9,259,231 B2 | 2/2016 | Navve et al. |
| 9,308,315 B2 | 4/2016 | Stubkjaer et al. |
| 9,597,160 B1 | 3/2017 | Gregg et al. |
| 9,907,563 B2 * | 3/2018 | Germain .............. A61M 3/0212 |
| 10,201,382 B2 | 2/2019 | Wiener et al. |
| 10,441,345 B2 | 10/2019 | Aldridge et al. |
| 12,016,626 B2 | 6/2024 | Shelton et al. |
| 12,023,096 B2 | 7/2024 | Shelton et al. |
| 12,059,204 B2 | 8/2024 | Talbot et al. |
| 2003/0036751 A1 | 2/2003 | Anderson et al. |
| 2004/0229295 A1 | 11/2004 | Marchitto et al. |
| 2005/0222535 A1 | 10/2005 | Uesugi et al. |
| 2006/0047185 A1 * | 3/2006 | Shener .................... A61B 1/015 |
| | | 600/156 |
| 2006/0264995 A1 | 11/2006 | Fanton et al. |
| 2007/0016114 A1 | 1/2007 | Buchholtz et al. |
| 2007/0073279 A1 | 3/2007 | Rowe et al. |
| 2008/0154185 A1 | 6/2008 | Blight |
| 2008/0300662 A1 | 12/2008 | Taylor |
| 2009/0058996 A1 | 3/2009 | Mitsuhashi |
| 2009/0156900 A1 | 6/2009 | Robertson |
| 2010/0004510 A1 | 1/2010 | Kuroshima |
| 2010/0049119 A1 * | 2/2010 | Norman ................ A61M 3/022 |
| | | 604/31 |
| 2010/0076304 A1 | 3/2010 | Teramura |
| 2011/0082449 A1 | 4/2011 | Melsky et al. |
| 2011/0237880 A1 | 9/2011 | Hamel et al. |
| 2012/0116168 A1 | 5/2012 | Moellstam et al. |
| 2013/0303852 A1 | 11/2013 | Hiraga et al. |
| 2015/0119645 A1 * | 4/2015 | Baldwin ................ A61B 17/22 |
| | | 600/114 |
| 2015/0133728 A1 | 5/2015 | Finkman et al. |
| 2015/0216394 A1 | 8/2015 | Toyoda |
| 2015/0230864 A1 | 8/2015 | Xuan et al. |
| 2015/0289937 A1 | 10/2015 | Chia et al. |
| 2015/0320303 A1 | 11/2015 | Kawase |
| 2015/0320433 A1 | 11/2015 | Navve et al. |
| 2015/0342682 A1 | 12/2015 | Bowe |
| 2016/0022126 A1 | 1/2016 | Ramesh et al. |
| 2016/0022289 A1 | 1/2016 | Wan |
| 2016/0135894 A1 | 5/2016 | Finkman et al. |
| 2016/0157954 A1 | 6/2016 | Sagon et al. |
| 2016/0206805 A1 | 7/2016 | Hassidov et al. |
| 2016/0250075 A1 | 9/2016 | Kawai et al. |
| 2017/0112572 A1 | 4/2017 | Shazly et al. |
| 2017/0215989 A1 | 8/2017 | Gregg et al. |
| 2017/0220754 A1 | 8/2017 | Harrah et al. |
| 2017/0325890 A1 | 11/2017 | Chia et al. |
| 2018/0084980 A1 | 3/2018 | Watanabe et al. |
| 2018/0168439 A1 | 6/2018 | Hibbs et al. |
| 2018/0289394 A1 * | 10/2018 | Shah ................ A61B 17/320016 |
| 2018/0325622 A1 | 11/2018 | Groves, Jr. et al. |
| 2019/0008545 A1 | 1/2019 | Stulen et al. |
| 2019/0134279 A1 | 5/2019 | Benamou et al. |
| 2019/0247566 A1 | 8/2019 | Hassidov et al. |
| 2019/0282073 A1 | 9/2019 | Truckai |
| 2020/0000522 A1 | 1/2020 | Chia et al. |
| 2020/0187768 A1 | 6/2020 | Shelton et al. |
| 2020/0330157 A1 | 10/2020 | Junger et al. |
| 2021/0045811 A1 | 2/2021 | Shelton et al. |
| 2021/0045812 A1 | 2/2021 | Talbot et al. |
| 2021/0220529 A1 * | 7/2021 | Wang .................... A61M 1/772 |
| 2021/0236728 A1 * | 8/2021 | Fanning .............. A61B 1/00066 |
| 2021/0244267 A1 | 8/2021 | Shtul et al. |
| 2024/0252245 A1 | 8/2024 | Shelton et al. |
| 2024/0261026 A1 | 8/2024 | Shelton et al. |
| 2024/0299093 A1 | 9/2024 | Talbot et al. |

(56) References Cited

U.S. PATENT DOCUMENTS

FOREIGN PATENT DOCUMENTS

| | | | |
|---|---|---|---|
| CA | 2734120 C * | 9/2016 | ............. A61B 17/32 |
| CN | 1249162 A | 4/2000 | |
| CN | 101273915 A | 10/2008 | |
| CN | 104619281 A | 5/2015 | |
| CN | 105682535 A | 6/2016 | |
| CN | 106232037 A | 12/2016 | |
| CN | 106456368 A | 2/2017 | |
| CN | 107106236 A | 8/2017 | |
| CN | 111683580 A | 9/2020 | |
| CN | 111683617 A | 9/2020 | |
| CN | 115175626 A | 10/2022 | |
| CN | 115334982 A | 11/2022 | |
| CN | 111683617 B | 6/2024 | |
| CN | 118593117 A | 9/2024 | |
| CN | 111683580 | 12/2024 | |
| DE | 19840346 A1 | 4/2000 | |
| DE | 112021001260 T5 | 12/2022 | |
| DE | 112021001396 T5 | 12/2022 | |
| EP | 0048410 A1 | 3/1982 | |
| EP | 1086674 A1 | 3/2001 | |
| EP | 3429453 A1 | 1/2019 | |
| EP | 3749242 A4 | 11/2021 | |
| EP | 3749167 B1 | 11/2024 | |
| JP | S5971736 A | 4/1984 | |
| JP | H03207371 A | 9/1991 | |
| JP | H08201026 A | 8/1996 | |
| JP | 2003210485 A | 7/2003 | |
| JP | 2005192924 A | 7/2005 | |
| JP | 2007014768 A | 1/2007 | |
| JP | 2007244679 A | 9/2007 | |
| JP | 2009506817 A | 2/2009 | |
| JP | 2009213589 A | 9/2009 | |
| JP | 2010075314 A | 4/2010 | |
| JP | 2016043178 A | 4/2016 | |
| JP | 2016515441 A | 5/2016 | |
| JP | 2016533830 A | 11/2016 | |
| JP | 2017500172 A | 1/2017 | |
| JP | 2017080348 A | 5/2017 | |
| JP | 2017522058 A | 8/2017 | |
| JP | 2019093138 A | 6/2019 | |
| JP | 7374911 B2 | 10/2023 | |
| JP | 7460526 B2 | 4/2024 | |
| JP | 7498287 B2 | 6/2024 | |
| JP | 7524336 B2 | 7/2024 | |
| KR | 102712427 B1 | 9/2024 | |
| MX | 2020008318 A | 1/2021 | |
| WO | WO-2011032165 A2 | 3/2011 | |
| WO | WO-2013099507 A1 | 7/2013 | |
| WO | WO-2015029039 A1 | 3/2015 | |
| WO | WO-2015069387 A1 | 5/2015 | |
| WO | WO-2017132365 A1 | 8/2017 | |
| WO | WO-2019157247 A1 | 8/2019 | |
| WO | WO-2019157406 A1 | 8/2019 | |
| WO | WO-2019157247 A9 | 4/2020 | |
| WO | WO-2019157409 A9 | 5/2020 | |
| WO | WO-2021173775 A1 | 9/2021 | |
| WO | WO-2021173791 A1 | 9/2021 | |

OTHER PUBLICATIONS

"International Application Serial No. PCT/US2021/019568, Written Opinion mailed May 14, 2021", 5 pgs.
"International Application Serial No. PCT/US2021/019599, International Search Report mailed May 19, 2021", 5 pgs.
"International Application Serial No. PCT/US2021/019599, Written Opinion mailed May 19, 2021", 5 pgs.
"European Application Serial No. 19750838.5, Response filed Mar. 13, 2021", 17 pgs.
"European Application Serial No. 19750915.1, Response filed Mar. 16, 2021", 9 pgs.
"International Application Serial No. PCT/US2019/017153, International Search Report mailed Apr. 30, 2019", 2 pgs.
"International Application Serial No. PCT/US2019/017153, Written Opinion mailed Apr. 30, 2019", 6 pgs.
"International Application Serial No. PCT/US2019/017391, International Preliminary Report on Patentability mailed Aug. 20, 2020", 8 pgs.
"International Application Serial No. PCT/US2019/017391, International Search Report mailed May 1, 2019", 3 pgs.
"International Application Serial No. PCT/US2019/017391, Written Opinion mailed May 1, 2019", 5 pgs.
"European Application Serial No. 19750838.5, Extended European Search Report mailed Oct. 1, 2021", 8 pgs.
"European Application Serial No. 19750915.1, Extended European Search Report mailed Nov. 22, 2021", 8 pgs.
U.S. Appl. No. 16/803,612, filed Feb. 27, 2020, Endoscope Unclogging System and Method.
U.S. Appl. No. 16/968,801, filed Aug. 10, 2020, System, Method and Computer-Readable Storage Device for Controlling Laser Light Source of Lithotripsy Device.
U.S. Appl. No. 16/968,800, filed Aug. 10, 2020, Medical Laser Apparatus and System.
"U.S. Appl. No. 16/803,612, Non Final Office Action mailed Mar. 7, 2022", 38 pgs.
"Korean Application Serial No. 10-2020-7026082, Voluntary Amendment Filed Jan. 11, 2022", w/English Claims, 15 pgs.
"U.S. Appl. No. 16/803,612, Examiner Interview Summary mailed Jun. 3, 2022", 3 pgs.
"U.S. Appl. No. 16/803,612, Final Office Action mailed Sep. 14, 2022", 34 pgs.
"U.S. Appl. No. 16/803,612, Response filed May 31, 2022 to Non Final Office Action mailed Mar. 7, 2022", 25 pgs.
"European Application Serial No. 19750838.5, Response filed Apr. 28, 2022 to Communication pursuant to Rules 70(2) and 70a(2) EPC mailed Oct. 19, 2021", 16 pgs.
"European Application Serial No. 19750838.5, Response filed Apr. 28, 2022 to Extended European Search Report mailed Oct. 1, 2021", 16 pgs.
"European Application Serial No. 19750915.1, Response filed Jun. 9, 2022 to Extended European Search Report mailed Nov. 22, 2021", 10 pgs.
"International Application Serial No. PCT/US2021/019568, International Preliminary Report on Patentability mailed Sep. 9, 2022", 7 pgs.
"International Application Serial No. PCT/US2021/019599, International Preliminary Report on Patentability mailed Sep. 9, 2022", 7 pgs.
"U.S. Appl. No. 16/803,612, Advisory Action mailed Dec. 1, 2022", 3 pgs.
"U.S. Appl. No. 16/803,612, Examiner Interview Summary mailed Mar. 28, 2023", 3 pgs.
"U.S. Appl. No. 16/803,612, Examiner Interview Summary mailed Nov. 8, 2022", 3 pgs.
"U.S. Appl. No. 16/803,612, Non Final Office Action mailed Dec. 28, 2022", 32 pgs.
"U.S. Appl. No. 16/803,612, Response filed Mar. 23, 2023 to Non Final Office Action mailed Dec. 28, 2022", 14 pgs.
"U.S. Appl. No. 16/803,612, Response filed Nov. 8, 2022 to Final Office Action mailed Sep. 14, 2022", 18 pgs.
"U.S. Appl. No. 16/803,612, Response filed Dec. 9, 2022 to Advisory Action mailed Dec. 1, 2022", 17 pgs.
"U.S. Appl. No. 16/968,800, Restriction Requirement mailed Apr. 5, 2023", 5 pgs.
"Indian Application Serial No. 202247046058, First Examination Report mailed Apr. 11, 2023", 6 pgs.
"Japanese Application Serial No. 2020-542770, Examiners Decision of Final Refusal mailed Feb. 27, 2023", w/ English Translation, 7 pgs.
"Japanese Application Serial No. 2020-542770, Notification of Reasons for Refusal mailed Nov. 14, 2022", w/ English translation, 14 pgs.
"Japanese Application Serial No. 2020-542770, Response filed Feb. 10, 2023 to Notification of Reasons for Refusal mailed Nov. 14, 2022", with machine translation, 24 pgs.

(56) References Cited

OTHER PUBLICATIONS

"Japanese Application Serial No. 2020-542995, Notification of Reasons for Rejection mailed Nov. 7, 2022", w/ English Translation, 9 pgs.
"U.S. Appl. No. 16/803,612, Advisory Action mailed Oct. 5, 2023", 3 pgs.
"U.S. Appl. No. 16/803,612, Response filed Sep. 25, 2023 to Final Office Action mailed Jul. 24, 2023", 15 pgs.
"U.S. Appl. No. 16/803,612, Response filed Oct. 24, 2023 to Advisory Action mailed Oct. 5, 2023", 14 pgs.
"U.S. Appl. No. 16/968,800, Response filed Sep. 21, 2023 to Non Final Office Action mailed Jun. 21, 2023", 13 pgs.
"U.S. Appl. No. 16/968,801, Response filed Oct. 3, 2023 to Restriction Requirement mailed Aug. 3, 2023", 11 pgs.
"U.S. Appl. No. 16/803,612, Final Office Action mailed Jul. 24, 2023", 35 pgs.
"U.S. Appl. No. 16/968,800, Non Final Office Action mailed Jun. 21, 2023", 13 pgs.
"U.S. Appl. No. 16/968,800, Response filed May 23, 2023 to Restriction Requirement mailed Apr. 5, 2023", 8 pgs.
"U.S. Appl. No. 16/968,801, Restriction Requirement mailed Aug. 3, 2023", 9 pgs.
"Japanese Application Serial No. 2020-542770, Response filed Jun. 27, 2023 to Examiners Decision of Final Refusal mailed Feb. 27, 2023", with machine translation, 23 pgs.
"Japanese Application Serial No. 2020-542995, Notification of Reasons for Refusal mailed May 22, 2023", w/ English translation, 8 pgs.
"Indian Application Serial No. 202247046058, Response filed Oct. 4, 2023 to Office Action mailed Apr. 11, 2023", 24 pgs.
"Japanese Application Serial No. 2020-542995, Response filed Sep. 7, 2023 to Notification of Reasons for Refusal mailed May 22, 2023", w/ english claims, 9 pgs.
"Japanese Application Serial No. 2022-551708, Notification of Reasons for Refusal mailed Aug. 28, 2023", w/ English Translation, 9 pgs.
"Japanese Application Serial No. 2022-551708, Response filed Oct. 13, 2023 to Notification of Reasons for Refusal mailed Aug. 28, 2023", with English claims, 12 pgs.
"Mexican Application Serial No. MX/a/2020/008318, Office Action mailed Aug. 31, 2023", with machine translation, 9 pgs.
"Australian Application Serial No. 2019216954, First Examination Report mailed Oct. 23, 2023", 4 pgs.
"Australian Application Serial No. 2019217992, First Examination Report mailed Nov. 22, 2023", 4 pgs.
"Canadian Application Serial No. 3,169,535, Examiners Rule 86(2) Requisition mailed Sep. 29, 2023", 4 pgs.
"Canadian Application Serial No. 3,169,549, Examiners Rule 86(2) Report mailed Sep. 29, 2023", 4 pgs.
"Chinese Application Serial No. 201980012090.7, Office Action mailed Nov. 3, 2023", W/English Translation, 25 pgs.
"Chinese Application Serial No. 201980012090.7, Response filed Dec. 27, 2023 to Office Action mailed Nov. 3, 2023", with English claims, 16 pgs.
"Japanese Application Serial No. 2022-551714, Notification of Reasons for Refusal mailed Oct. 23, 2023", w/ English Translation, 15 pgs.
"Japanese Application Serial No. 2022-551714, Response filed Dec. 18, 2023 to Notification of Reasons for Refusal mailed Oct. 23, 2023", with English claims, 10 pgs.
"Japanese Application Serial No. 2023-105314, Voluntary Amendment mailed Dec. 15, 2023", with machine translation, 9 pgs.
"Korean Application Serial No. 10-2020-7026082, Notice of Preliminary Rejection mailed Dec. 21, 2023", with machine translation, 6 pgs.
"Mexican Application Serial No. MX/a/2020/008318, Response filed Nov. 16, 2023 to Office Action mailed Aug. 31, 2023", with machine translation, 23 pgs.
"U.S. Appl. No. 16/803,612, Corrected Notice of Allowability mailed Feb. 28, 2024", 6 pgs.
"U.S. Appl. No. 16/803,612, Examiner Interview Summary mailed Feb. 8, 2024", 3 pgs.
"U.S. Appl. No. 16/803,612, Notice of Allowance mailed Feb. 14, 2024", 9 pgs.
"U.S. Appl. No. 16/803,612, Response filed Feb. 5, 2024 to Non Final Office Action mailed Nov. 8, 2023", 15 pgs.
"U.S. Appl. No. 16/968,800, Examiner Interview Summary mailed Jan. 31, 2024", 3 pgs.
"U.S. Appl. No. 16/968,800, Notice of Allowance mailed Feb. 14, 2024", 8 pgs.
"U.S. Appl. No. 16/968,800, Response filed Jan. 25, 2024 to Final Office Action mailed Nov. 30, 2023", 12 pgs.
"Australian Application Serial No. 2019216954, Response filed Jan. 8, 2024 to First or Subsequent Examiner Report mailed Oct. 23, 2023", 22 pgs.
"Canadian Application Serial No. 3,169,535, Response filed Jan. 25, 2024 to Examiners Rule 86(2) Requisition mailed Sep. 29, 2023", 16 pgs.
"Canadian Application Serial No. 3,169,549, Response filed Jan. 29, 2024 to Examiners Rule 86(2) Report mailed Sep. 29, 2023", 19 pgs.
"Chinese Application Serial No. 201980012086.0, First Office Action mailed Jan. 15, 2024", with English translation, 21 pgs.
"European Application Serial No. 19750838.5, Communication Pursuant to Article 94(3) EPC mailed Feb. 8, 2024", 3 pgs.
"Japanese Application Serial No. 2022-551708, Examiners Decision of Final Refusal mailed Jan. 15, 2024", W/English Translation, 6 pgs.
"Korean Application Serial No. 2020-7025950, Notice of Preliminary Rejection mailed Jan. 30, 2024", with machine translation, 16 pgs.
"U.S. Appl. No. 16/803,612, Non Final Office Action mailed Nov. 8, 2023", 26 pgs.
"U.S. Appl. No. 16/968,800, Final Office Action mailed Nov. 30, 2023", 13 pgs.
"U.S. Appl. No. 16/968,801, Non Final Office Action mailed Dec. 14, 2023", 16 pgs.
"Iteration", Merriam-Webster.com Dictionary, Merriam-Webster, [Online] Retrieved from the internet: <https://www.merriam-webster.com/dictionary/iteration>, (Dec. 2023), 1 pg.
"U.S. Appl. No. 16/803,612, Corrected Notice of Allowability mailed Apr. 23, 2024", 7 pgs.
"U.S. Appl. No. 16/968,800, Corrected Notice of Allowability mailed Jun. 3, 2024", 2 pgs.
"U.S. Appl. No. 16/968,801, Examiner Interview Summary mailed Mar. 15, 2024", 2 pgs.
"U.S. Appl. No. 16/968,801, Notice of Allowance mailed Mar. 27, 2024", 9 pgs.
"U.S. Appl. No. 16/968,801, Response filed Mar. 13, 2024 to Non Final Office Action mailed Dec. 14, 2023", 15 pgs.
"Australian Application Serial No. 2019217992, Response filed Mar. 26, 2024 to First Examination Report mailed Nov. 22, 2023", 21 pgs.
"Australian Application Serial No. 2019217992, Response filed May 24, 2024 to Subsequent Examiners Report mailed Apr. 8, 2024", 17 pgs.
"Australian Application Serial No. 2019217992, Subsequent Examiners Report mailed Apr. 8, 2024", 2 pgs.
"Chinese Application Serial No. 201980012086.0, Response filed May 8, 2024 to Office Action mailed Jan. 15, 2024", w/ English Claims, 11 pgs.
"European Application Serial No. 19750838.5, Response filed Jun. 7, 2024 to Communication Pursuant to Article 94(3) EPC mailed Feb. 8, 2024", 3 pgs.
"Japanese Application Serial No. 2022-551708, Response filed Mar. 27, 2024 to Examiners Decision of Final Refusal mailed Jan. 15, 2024", w/ english claims, 17 pgs.
"Japanese Application Serial No. 2022-551714, Notification of Reasons for Rejection mailed Mar. 4, 2024", W/English Translation, 8 pgs.
"Japanese Application Serial No. 2022-551714, Response filed May 31, 2024 to Notification of Reasons for Rejection mailed Mar. 4, 2024", W/English Claims, 8 pgs.

(56) References Cited

OTHER PUBLICATIONS

"Japanese Application Serial No. 2024-045080, Notification of Reasons for Refusal mailed May 27, 2024", w/ English Translation, 13 pgs.

"Japanese Application Serial No. 2024-51659, Voluntary Amendment filed May 17, 2024", with machine translation, 9 pgs.

"Korean Application Serial No. 10-2020-7026082, Response filed Feb. 16, 2024 to Notice of Preliminary Rejection mailed Dec. 21, 2023", w/ english claims, 24 pgs.

"Korean Application Serial No. 2020-7025950, Response filed Mar. 28, 2024 to Notice of Preliminary Rejection mailed Jan. 30, 2024", w/ current English claims, 18 pgs.

"Mexican Application Serial No. MX/a/2020/008321, Office Action mailed Apr. 16, 2024", with machine translation, 7 pgs.

"Mexican Application Serial No. MX/a/2020/008321, Response filed Jun. 6, 2024 to Office Action mailed Apr. 16, 2024", with machine translation, 13 pgs.

"U.S. Appl. No. 16/968,801, Corrected Notice of Allowability mailed Jul. 11, 2024", 2 pgs.

"Japanese Application Serial No. 2024-045080, Examiners Decision of Final Refusal mailed Nov. 18, 2024", w English translation, 7 pgs.

"Canadian Application Serial No. 3,169,535, Response filed Dec. 16, 2024 to Examiners Rule 86(2) Report mailed Aug. 16, 2024", w claims, 13 pgs.

"Canadian Application Serial No. 3,169,549, Response filed Dec. 17, 2024 to Examiners Rule 86(2) Report mailed Aug. 26, 2024", w claims, 25 pgs.

"Canadian Application Serial No. 3,169,535, Examiners Rule 86(2) Report mailed Aug. 16, 2024", 4 pgs.

"Canadian Application Serial No. 3,169,549, Examiners Rule 86(2) Report mailed Aug. 26, 2024", 4 pgs.

"Japanese Application Serial No. 2023-105314, Notification of Reasons for Rejection mailed Aug. 5, 2024", W/English Translation, 12 pgs.

"Japanese Application Serial No. 2024-045080, Response filed Sep. 11, 2024 to Notification of Reasons for Refusal mailed May 27, 2024", w/ current English claims, 12 pgs.

"European Application Serial No. 19750838.5, Communication Pursuant to Article 94(3) EPC mailed Nov. 13, 2024", 4 pgs.

"Japanese Application Serial No. 2023-105314, Response filed Nov. 1, 2024 to Notification of Reasons for Rejection mailed Aug. 5, 2024", w/ current English claims, 15 pgs.

* cited by examiner

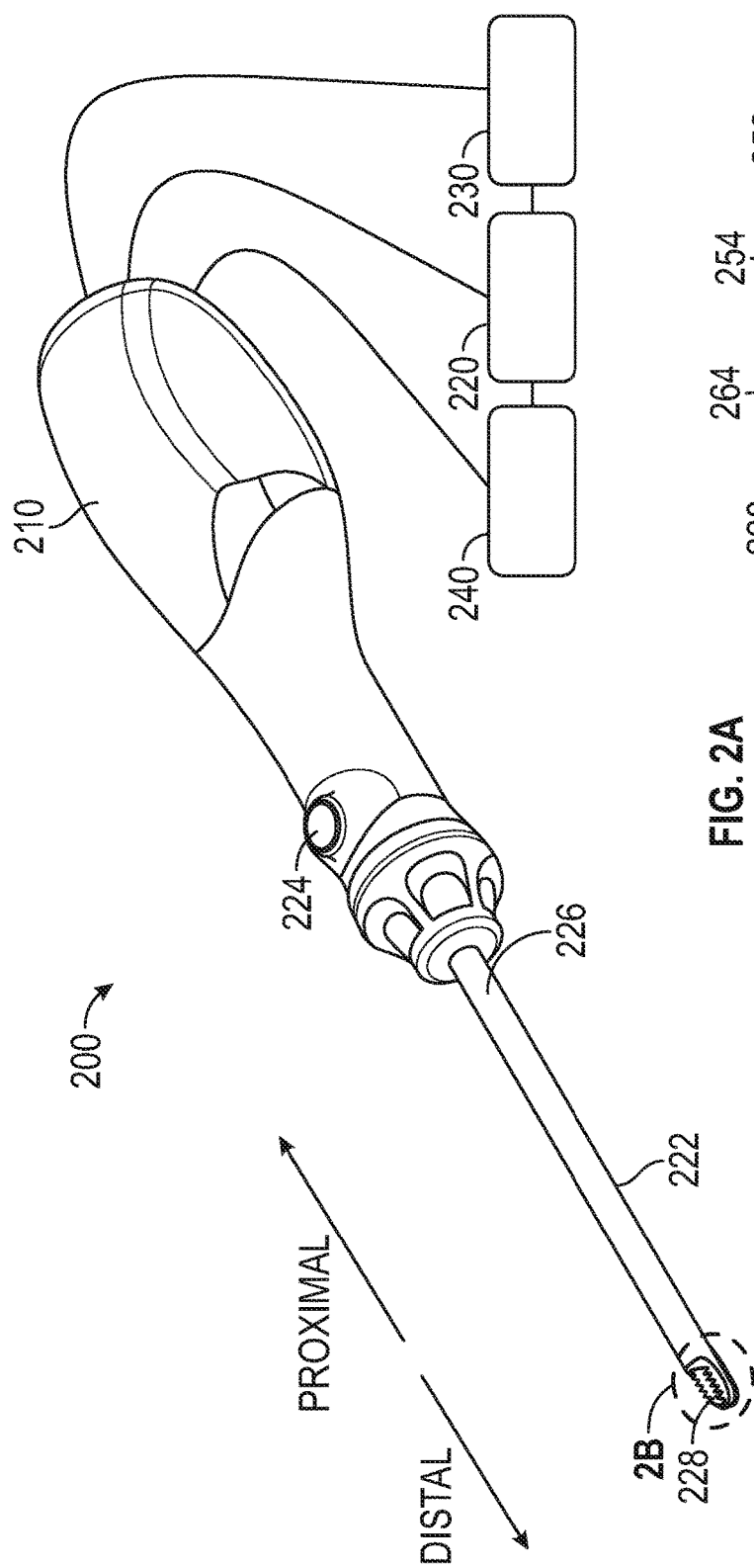
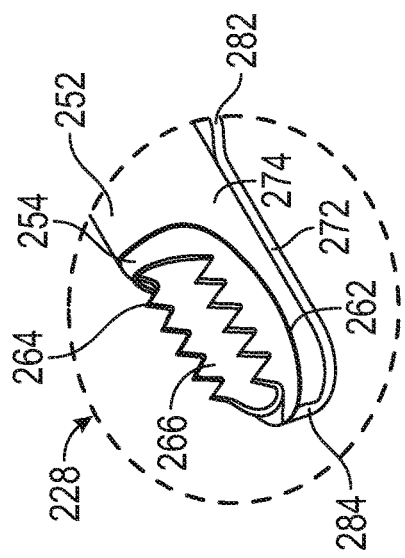
FIG. 2A
FIG. 2B

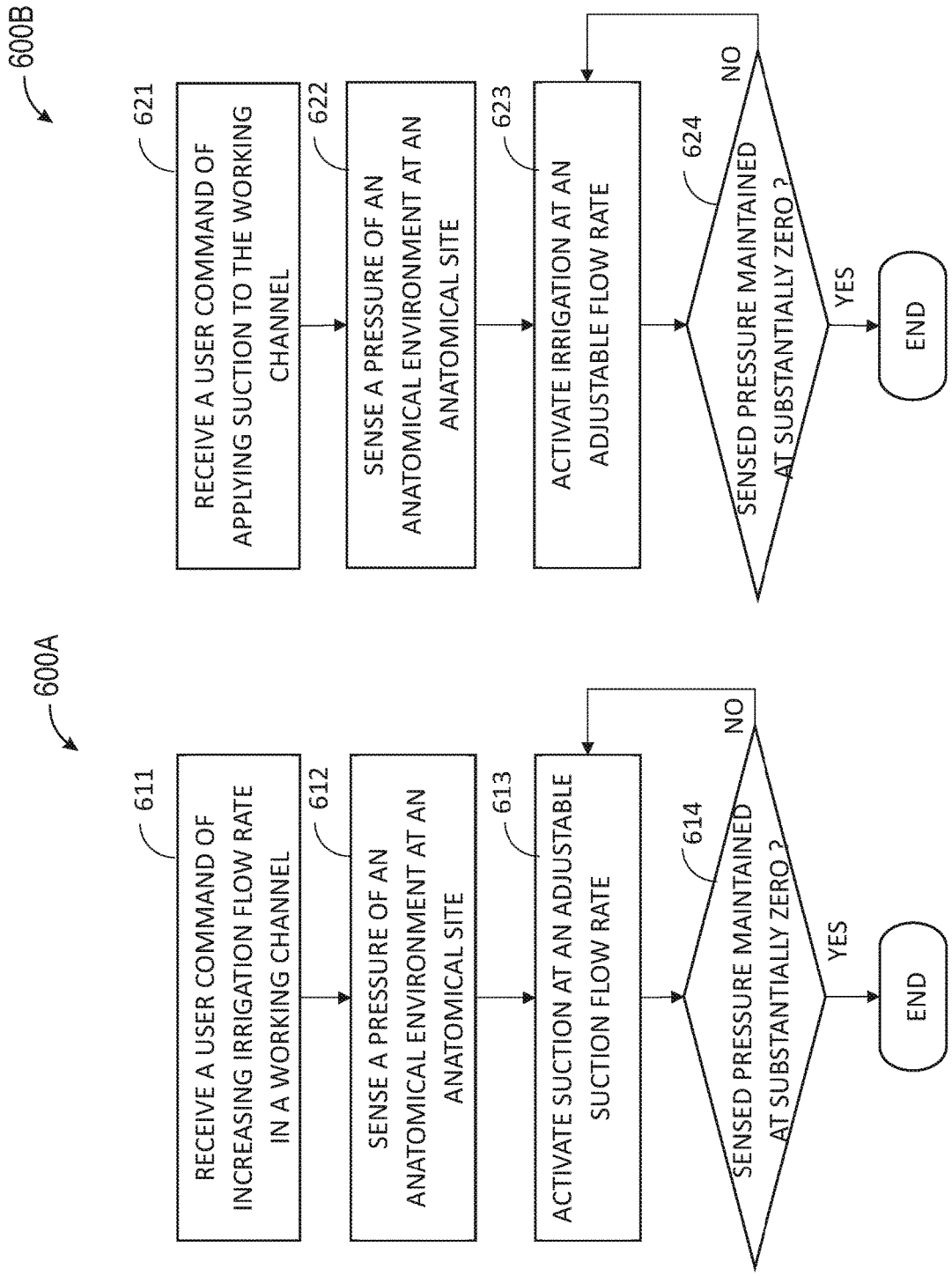

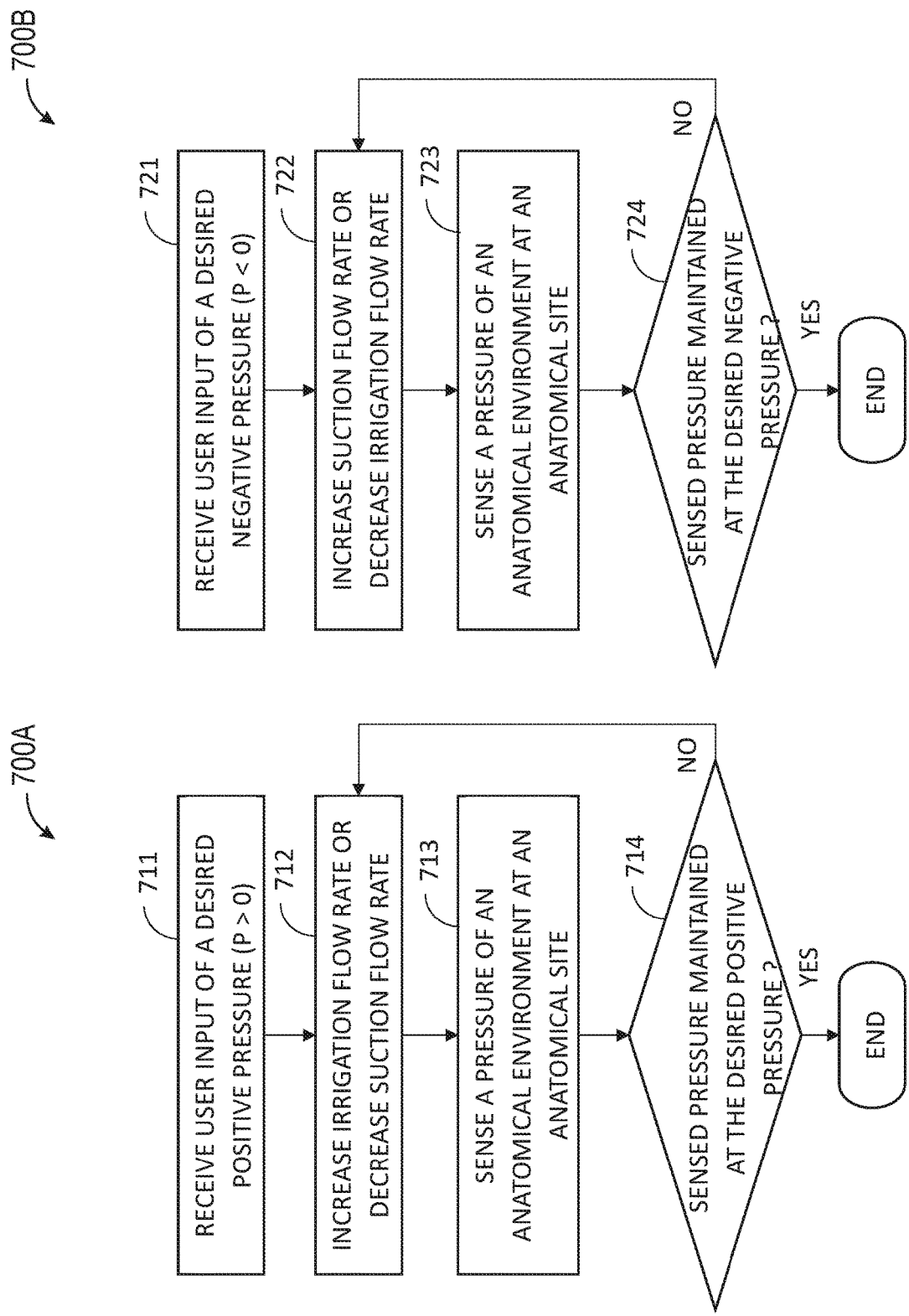

SUCTION AND IRRIGATION CONTROL SYSTEM AND METHOD

CLAIM OF PRIORITY

This application is a Continuation-in-Part and claims benefit of Shelton et al., International Patent Application Serial Number PCT/US2019/017391, titled "SYSTEM, METHOD AND COMPUTER-READABLE STORAGE DEVICE FOR CONTROLLING LASER LIGHT SOURCE OF LITHOTRIPSY DEVICE," filed Feb. 8, 2019, which claims the benefit of priority, and incorporates by reference the entirety, of U.S. Provisional Application No. 62/628,513 filed on Feb. 9, 2018, the benefit of each of which is hereby presently claimed, and the entirety of each of which is hereby incorporated by reference herein.

CROSS REFERENCE TO RELATED APPLICATION

This application is related to commonly assigned U.S. patent application, entitled "ENDOSCOPE UNCLOGGING SYSTEM AND METHOD", filed on Feb. 27, 2020, which is incorporated by reference in its entirety herein.

TECHNICAL FIELD

This document relates generally to an endoscopy system, and more specifically relates to a suction and irrigation system to keep the in situ pressure of an anatomical environment at the anatomical site under control during an endoscopic procedure.

BACKGROUND

Endoscopes are typically used to provide access to an internal location of a patient so that a doctor is provided with visual access. Some endoscopes are used in minimally invasive surgery to remove unwanted tissue or foreign objects from the body of the patient. For example, an endoscopic tissue removal device is an instrument used by a clinician to remotely access necrotic, cancerous, damaged, infected or otherwise unwanted soft tissue, bone, or other anatomical structures at an anatomical site, excise said unwanted matters from the adjacent anatomy, and transport them away from the anatomical site. A nephroscope is used by a clinician to inspect the renal system, and to perform various procedures under direct visual control. For example, percutaneous nephrolithotomy (PCNL) is procedure involving placement of a nephroscope through the patient's flank into the renal pelvis. Calculi or mass from various regions of a body including, for example, urinary system, gallbladder, nasal passages, gastrointestinal tract, stomach, or tonsils, can be visualized and extracted. Calculi of larger sizes can be ablated into smaller fragments using oscillating forces such as shock waves, ultrasonic energy (via a specialized device such as an ultrasonic lithotripter), or lasers.

Some endoscopes have suction channels (also known as aspiration channels) to transport resected tissue, calculi (e.g., stones or stone fragments in various stone-forming regions) and mass, among other unwanted matters. A flow of irrigation agent (e.g., saline solution) can be introduced to the anatomical site through an irrigation channel in the endoscope during the procedure. The irrigation fluid can facilitate removal of the tissue debris, stone fragments, and other unwanted matters through the suction channel. The irrigation fluid can also help maintain a clear visibility of the anatomical environment for the clinician performing the procedure. Additionally, the irrigation flow has a cooling effect on the endoscopic tissue removal device and can help dissipate the heat generated during ablation of calculi (e.g., kidney stones).

Pressure of the anatomical environment at the anatomical site, such as the anatomy being operated on, may vary during the endoscopic procedure. For example, application of a flow or irrigation fluid or suction pressure can fluctuate the pressure of the anatomical environment, which may have harmful effects to the internal organs. It is desirable to keep the pressure of the anatomical environment under control during the endoscopic procedure to avoid or reduce pressure-related harm to the internal organs.

SUMMARY

The present document describes systems and methods of maintaining in situ pressure of an anatomical environment at an anatomical site during an endoscopic procedure. According to one aspect of the present document, a pressure control system comprises a user input configured to receive from a user a desired pressure to be applied to the anatomical environment, or a desired flow condition in a working channel of an endoscope that corresponds to the desired pressure. The system comprises a pressure sensor configured to sense a pressure of the anatomical environment, and a control module configured to adjust one or more of an irrigation flow rate or a suction flow rate of at least one working channel of the endoscope based on the sensed pressure to maintain the pressure of the anatomical environment at substantially a level of the desired pressure, or to maintain the desired flow condition in the working channel, during the endoscopic procedure.

Example 1 is a system for maintaining a pressure applied to an anatomical environment at an anatomical site in a patient during a procedure using a medical device. The system comprises: a user input configured to receive from a user a desired pressure to be applied to the anatomical environment at the anatomical site; a pressure sensor configured to sense a pressure of the anatomical environment at the anatomical site; and a control module configured to, based on the sensed pressure, control one or more of an irrigation flow rate or a suction flow rate through at least one working channel of the medical device to maintain the pressure of the anatomical environment at substantially a level of the desired pressure.

In Example 2, the subject matter of Example 1 optionally includes the user input that can be configured to receive a desired flow condition in the at least one working channel, the desired flow condition corresponding to the desired pressure to be applied to the anatomical environment; and the control module is configured to control one or more of an irrigation flow rate or a suction flow rate through at least one working channel of the medical device to maintain the desired flow condition.

In Example 3, the subject matter of any one or more of Examples 1-2 optionally include the control module that can be configured to: fluidly couple an irrigation source to the at least one working channel to provide an irrigation fluid thereto at an adjustable irrigation flow rate; and fluidly couple a suction source to the at least one working channel to supply a suction pressure thereto at an adjustable suction flow rate.

In Example 4, the subject matter of Example 3 optionally includes the at least one working channel that can include an irrigation channel and a suction channel, and wherein the control module is configured to provide the irrigation fluid to the irrigation channel at the adjustable irrigation flow rate, and to provide the suction pressure to the suction channel at the adjustable suction flow rate.

In Example 5, the subject matter of any one or more of Examples 1-4 optionally includes the user input that can be configured to receive a user command of increasing or decreasing one or more of the irrigation flow rate or the suction flow rate.

In Example 6, the subject matter of any one or more of Examples 1-5 optionally includes the desired pressure that can be a substantially net-zero pressure of the anatomical environment, and the control module that can be configured to: in response to an increase in the sensed pressure produced by an increase in the irrigation flow rate, increase the suction flow rate through the at least one working channel to substantially neutralize the increase in the sensed pressure; and in response to a decrease in the sensed pressure produced by an increase in the suction flow rate, increase the irrigation flow rate through the at least one working channel to substantially neutralize the decrease in the sensed pressure.

In Example 7, the subject matter of any one or more of Examples 1-5 optionally includes the desired pressure that can be a positive pressure of the anatomical environment, and the control module that can be configured to increase the irrigation flow rate or to decrease the suction flow rate through the at least one working channel until the sensed pressure reaches substantially a level of the desired positive pressure.

In Example 8, the subject matter of any one or more of Examples 1-5 optionally includes the desired pressure that can be a negative pressure of the anatomical environment, and the control module that can be configured to decrease the irrigation flow rate or to increase the suction flow rate through the at least one working channel until the sensed pressure reaches substantially a level of the desired negative pressure.

In Example 9, the subject matter of any one or more of Examples 1-8 optionally includes a tissue removal device at least partially insertable into the anatomical site, tissue removal device configured to illuminate at least a portion of the anatomical environment and surrounding environment, provide an image of the anatomical environment, resect unwanted tissue from the anatomical environment, and remove the resected tissue through the at least one working channel, and wherein the control module can be configured to adjust one or more of the irrigation flow rate or the suction flow rate to maintain the pressure of the anatomical environment at substantially a level of the desired pressure.

In Example 10, the subject matter of any one or more of Examples 8 optionally includes a nephroscope at least partially insertable into a portion of a urinary tract of the patient, the nephroscope configured to illuminate renal mass and surrounding environment, provide an image of the illuminated renal mass, break the renal mass into fragments, and remove the renal mass fragments through the at least one working channel; and the control module that can be configured to adjust one or more of the irrigation flow rate or the suction flow rate to maintain the pressure of the environment surrounding the renal mass at substantially a level of the desired pressure.

Example 11 is an endoscopic surgical system comprising: an endoscope including an imaging module, a surgical module, and at least one working channel configured to conduct an irrigation fluid or a suction pressure; a user input configured to receive from a user a desired pressure to be applied to an anatomical environment at an anatomical site; a pressure sensor configured to sense a pressure of the anatomical environment at the anatomical site; and a control module configured to, based on the sensed pressure, adjust one or more of an irrigation flow rate or a suction flow rate through the at least one working channel to maintain the pressure of the anatomical environment at substantially a level of the desired pressure.

In Example 12, the subject matter of Example 11 optionally includes: the at least one working channel that can include an irrigation channel and a suction channel; and the control module that can be configured to fluidly couple an irrigation source to the irrigation channel to provide an irrigation fluid thereto at an adjustable irrigation flow rate, and fluidly couple a suction source to the suction channel to supply a suction pressure thereto at an adjustable suction flow rate.

In Example 13, the subject matter of any one or more of Examples 11-12 optionally includes the user input that can be configured to receive a user command of increasing or decreasing one or more of the irrigation flow rate or the suction flow rate, and the desired pressure can be a substantially net-zero pressure, a positive pressure, or a negative pressure of the anatomical environment.

Example 14 is a method of maintaining a pressure applied to an anatomical environment at an anatomical site in a patient during a procedure using a medical device. The method comprises steps of: receiving, via a user input, a desired pressure to be applied to an anatomical environment at an anatomical site; sensing a pressure of the anatomical environment at the anatomical site via a pressure sensor; and based on the sensed pressure, adjusting one or more of an irrigation flow rate or a suction flow rate through the at least one working channel via a control module to maintain the pressure of the anatomical environment at substantially a level of the desired pressure.

In Example 15, the subject matter of Example 14 optionally includes steps of receiving a desired flow condition in the at least one working channel, the desired flow condition corresponding to the desired pressure to be applied to the anatomical environment; and adjusting one or more of the irrigation flow rate or the suction flow rate through the at least one working channel to maintain the desired flow condition.

In Example 16, the subject matter of any one or more of Examples 14-15 optionally include the at least one working channel that can include an irrigation channel and a suction channel. The method comprises steps: controlling an irrigation source to provide an irrigation fluid at the adjustable irrigation in irrigation channel; and controlling a suction source to provide a suction pressure at an adjustable suction flow rate through the suction channel.

In Example 17, the subject matter of Example 16 optionally includes receiving from the user input a user command of increasing or decreasing one or more of the irrigation flow rate or the suction flow rate.

In Example 18, the subject matter of any one or more of Examples 14-17 optionally include the desired pressure that can be a substantially net-zero pressure of the anatomical environment, and adjusting the one or more of the irrigation flow rate or the suction flow rate can include steps of: in response to an increase in the sensed pressure produced by an increase in the irrigation flow rate, increasing the suction flow rate through the at least one working channel to substantially neutralize the increase in the sensed pressure; and in response to a decrease in the sensed pressure produced by an increase in the suction flow rate, increasing the irrigation flow rate through the at least one working channel to substantially neutralize the decrease in the sensed pressure.

In Example 19, the subject matter of any one or more of Examples 14-17 optionally includes the desired pressure that can be a positive pressure of the anatomical environment, and adjusting the one or more of the irrigation flow rate or the suction flow rate can include increasing the irrigation flow rate or decreasing the suction flow rate through the at least one working channel until the sensed pressure reaches substantially a level of the desired positive pressure.

In Example 20, the subject matter of any one or more of Examples 14-17 optionally includes the desired pressure that can be a negative pressure of the anatomical environment, and adjusting the one or more of the irrigation flow rate or the suction flow rate can include decreasing the irrigation flow rate or increasing the suction flow rate through the at least one working channel until the sensed pressure reaches substantially a level of the desired negative pressure.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 2A-2B are diagrams illustrating a powered tissue removal device 200 that may be used in the system as described in reference to FIG. 1.

FIGS. 6A-6B are flow charts illustrating methods for maintaining a balanced environmental pressure of the anatomical environment during an endoscopic procedure.

FIGS. 7A-7B are flow charts illustrating methods for maintaining a desired positive pressure or a desired negative pressure of the anatomical environment during an endoscopic procedure.

DETAILED DESCRIPTION

An endoscope comprises a tubular portion insertable into an interior of an organ or a cavity of the body to assist in diagnosis or treatment. One or more working channels (e.g., a suction channel and/or an irrigation channel) can be disposed inside, and extend along a length of, the tubular portion to provide a flow or irrigation fluid or suction pressure during an endoscopic procedure. Irrigation and suction can facilitate transportation of unwanted matters produced during the endoscopic procedure, such as tissue debris, calculi and mass, or body fluid, among others.

Suction through a working channel in an endoscope may result in a negative pressure change at the anatomical site. Application of irrigation fluid through a working channel in an endoscope may result in a positive pressure change at the anatomical site. Negative and positive pressure changes, if not properly controlled, may be harmful to internal organs exposed to the anatomical site. For example, while the body can regulate some positive pressure changes, many organs are relatively defenseless to negative pressure changes.

The present inventor has recognized an unmet need of an endoscopic system capable of monitoring the pressure of the anatomical environment at the anatomical site, stabilizing the pressure of the anatomical environment during the procedure, and enabling a user to manually control suction flow and/or irrigation flow so as to protect internal organs from pressure-related harm.

Disclosed herein are systems and methods of maintaining an in situ pressure of an anatomical environment at an anatomical site (e.g., an internal organ or the environment thereof) during an endoscopic procedure. According to one aspect of the present document, an irrigation and suction system includes a pressure sensor configured to sense a pressure of the anatomical environment, and a control module configured to adjust one or more of an irrigation flow rate or a suction flow rate of at least one working channel of the endoscope based on the sensed pressure. The control module can use a feedback control mechanism to keep the pressure change under control, such as to maintain the pressure of the anatomical environment at substantially a level of a desired pressure, or to maintain a desired flow condition in the working channel, during the endoscopic procedure.

The systems and methods according to various embodiments discussed in this document provide an improved solution to in situ pressure control during endoscopic procedures. The proposed solution, including controlled application of irrigation fluid and suction pressure, offers environmental stabilization of internal organs. The feedback control of pressure discussed herein offers users endoscopy without repeated insertion and removal of endoscope attachment and accessories, and can effectively reduce procedure time and increase patient safety.

Figure 1:
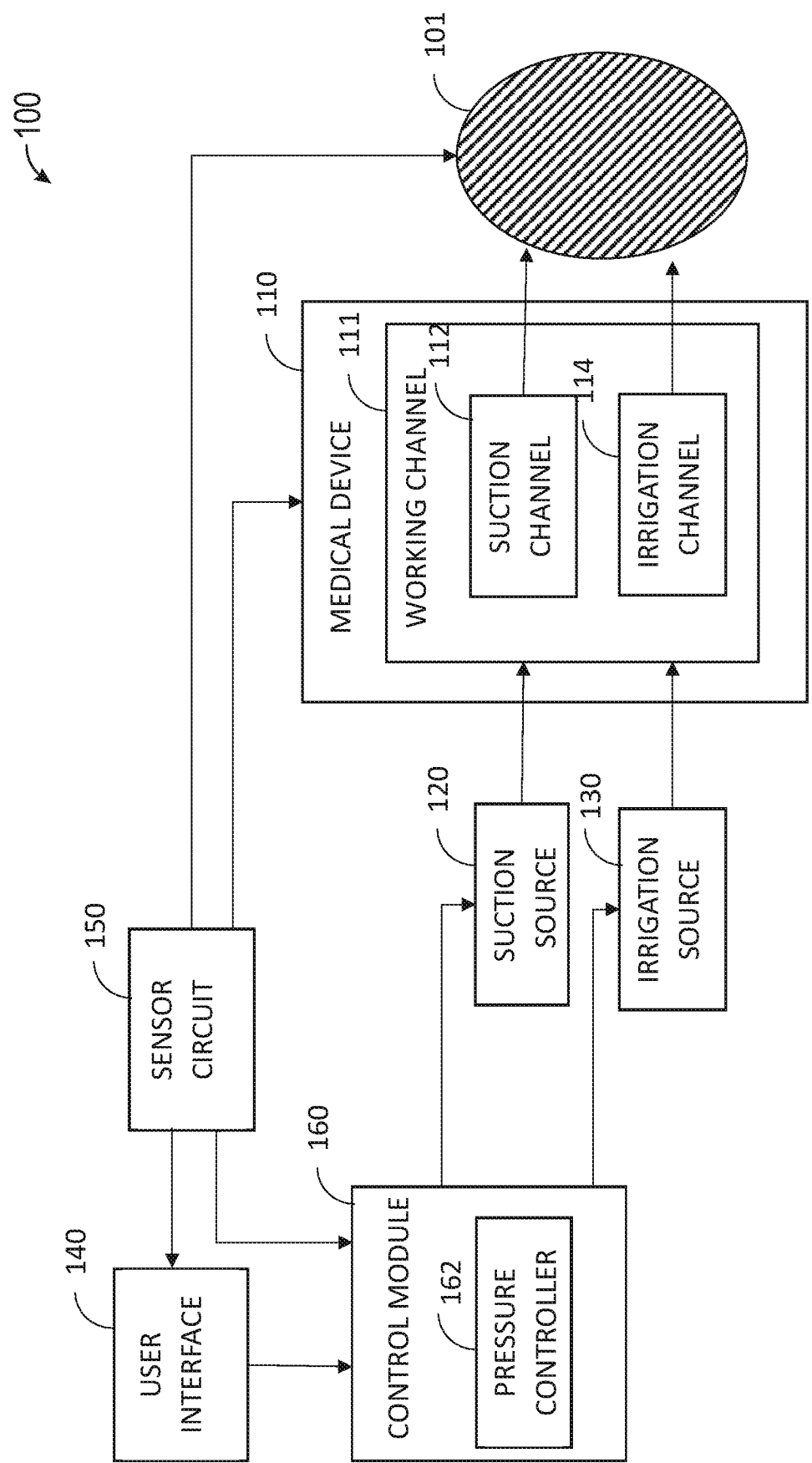
FIG. 1 is a block diagram illustrating an example of a system for maintaining an in situ pressure of an anatomical environment at an anatomical site at substantially a desired level during a minimally invasive procedure.

FIG. 1 is a block diagram illustrating an example of a system 100 for maintaining an in sill/pressure of an anatomical environment 101 at an anatomical site at substantially a desired level during a minimally invasive procedure. The system 100 may include a medical device 110 and optional component(s). The optional component(s) can include any of a suction source 120, an irrigation source 130, a user interface 140, a sensor circuit 150, or a control module 160. In various examples, the system 100 can have a modular design that provides enhanced flexibility to allow easy configuration and replacement of an individual component. In an example, the user interface 140, the sensor circuit 150, and the control module 160 can be included in a suction/irrigation control unit. The suction/irrigation control unit can be fluidly coupled to one or more the device 110, the suction source 120, or the irrigation source 130. The suction/irrigation control unit can adapt to different types of medical device and different types of irrigation source and suction source. Exemplary suction/irrigation control units are discussed below with reference to FIGS. 3A-3B. The suction/irrigation control unit can selectively activate or deactivate irrigation and/or suction through the working channel 111, and adjust one or more of an irrigation flow rate, irrigation fluid pressure, a suction flow rate, or suction pressure. By controlling suction and/or irrigation in accordance with various embodiments discussed herein, the pressure of the anatomical environment 101 can be maintained at a desired level during the procedure.

The medical device 110 can be used in diagnostic, analytical, or therapeutic applications, including, for example, minimally invasive surgeries such as endoscopic procedures. By way of example and not limitation, the medical device 110 may be used in joint surgery, plastic surgery, various otolaryngologic procedures, including but not limited to sinus surgery and tonsillectomy, or a combination thereof. The medical device 110 can be controlled by a user to perform a procedure in an organ in the anatomical environment 101 or to remove organ tissue. The controls of the medical device 110 may include a hand piece or indirect control, e.g., via a robotic surgery console or a user interface.

An example of the medical device 100 can include a tissue removal device comprising a blade assembly configured to rotate and/or reciprocate to excise unwanted tissue from target anatomy. The blade assembly may be driven by a motor powered by an energy source internal, or alternatively external, to the hand piece. The energy source may also fulfil other functions such as providing powered irrigation and suction to the medical device 110, as to be discussed below. Various blade assemblies can be used, including, for example, a shaver, a debrider, a blade, or a burr, among others. Depending on the blade assemblies used, the tissue removal device may function to shave, cut, abrade, or otherwise remove necrotic, cancerous, damaged, infected or otherwise unwanted soft tissue, bone, or other anatomical features or objects at or from the target anatomy. An exemplary tissue removal device is discussed below with reference to FIGS. 2A-2B.

Another example of the medical device 110 can include an endoscope. Examples of the endoscope can include a cystoscope for examining a urinary bladder, a nephroscope for examining a kidney, a bronchoscope for examining a bronchus, an arthroscope for examining joints, a colonoscope for examining a colon, a cholangioscope for examining biliary region (e.g., bile ducts), a duodenoscope for examining gastrointestinal region, or a laparoscope for examining abdomen or pelvis, among others. The endoscope may include a light source to illuminate the anatomical environment at the anatomical site, and an imaging module to produce images or video of the anatomical environment during the endoscopic procedure. Some endoscopes, such as an endoscopic tissue removal device, can include a tissue resection member configured to shave, cut, abrade, or otherwise remove portions of unwanted tissue from the target anatomy. The resected tissue debris can then be extracted from the anatomical site. Some endoscopes can include an ablation member configured to break or remove a foreign object, such as crystalline mineral structures, from the anatomical environment. For example, a nephroscope can be at least partially inserted into a kidney. Ultrasonic energy, electromagnetic shock waves, or lasers, among other energy modalities, may be delivered to kidney stones to break them into fragments or "stone dust", which can then be extracted from the anatomical site. An exemplary endoscope is discussed below with reference to FIGS. 3A-3B.

The medical device 110 can include one or more working channels 111 to transport the shaved, cut, resected, abraded, or removed tissue, bone, or the other anatomical features or objects, calculi and mass, body fluid at the anatomical site, and irrigation fluid, referred to herein collectively as "unwanted matters". The working channel 111 can be selectively coupled to one or more of the suction source 120 (such as via a suction port on the medical device 110) or the irrigation source 130 (such as via an irrigation port on the medical device 110).

The suction source 120 may function to pull, suck, draw, aspirate, or otherwise move or remove the unwanted matters from the anatomical site. The unwanted matters may be moved into a receptacle located at a proximal end of the medical device 110, inside the hand piece, or at a location away from the medical device 110. In an example, the hand piece may contain a container or reservoir for collecting, at least temporarily, the unwanted matters, before the hand piece being cleaned and the collected matter removed. The suction source 120 may perform the aforementioned functions by generating and applying vacuum, suction, or negative pressure to the working channel 111 of the medical device 110. In an example, the suction source 120 can be separate from the medical device 110, and connected thereto via one or more tubes, wires, or hoses. In another example, the suction source 120 can be included in or attached to the medical device 110. For example, the suction source 120 may be contained within the hand piece of a tissue removal device or an endoscope. The suction source may be powered by the energy source that also powers the medical device, or may be powered by its own energy source.

The irrigation source 130 may function to provide irrigation fluid to the working channel 111 to assist in the removal of unwanted matters (e.g., tissue debris or stone fragments) through the working channel 111. The irrigation fluid may also cool the tissue removal device or the resection elements during rotatory or reciprocated debridement or resection, and help dissipate the heat generated during stone fragmentation. The irrigation fluid may be gravity fed or pressurized. In an example, the irrigation source may comprise a bag that is elevated relative to the medical device 111 and the anatomical site to produce gravity-fed irrigation fluid. In another example, a pump may produce pressurized irrigation flow. The irrigation fluid can be provided from the irrigation source 130 or a location where the irrigation fluid is contained, to and through an external fluid supply tube, and drawn into the working channel 111. Under a suction pressure provided by the suction source 120, the irrigation fluid, along with the unwanted matters, can flow towards a proximal direction of the working channel 111 and removed from the anatomical site.

In an example, a single working channel 111 can be used for both irrigation and suction. The control module 160 can controllably activate irrigation and suction through the working channel 111 at separate times. In another example, the medical device 110 may include two or more separate working channels, such as a suction channel 112 and an irrigation channel 114, as illustrated in FIG. 1. The suction channel 112 can be controllably connected to the suction source 120 to conduct the unwanted matters being sucked therethrough. The irrigation channel 114 can be controllably connected to the irrigation source 130 to conduct irrigation fluid therethrough. In an example, the suction channel 112 can be controllably connected to the irrigation source 130. In an example, the irrigation channel 114 can be controllably connected to the suction source 120. Irrigation and suction according to various examples discussed herein can be used to assist in removing unwanted matters, maintaining the pressure of the anatomical environment at a desired level, and maintaining a desired flow condition in the working channel that corresponds to the desired pressure, among others.

In an example, the suction channel 112 and the irrigation channel 114 can be disposed in a parallel orientation along a length of a tubular portion of the hand piece of the medical device 110. In an example, the suction channel 112 and the irrigation channel 114 can be coaxially disposed with a common axis, such as in a nested configuration. In an example, the medical device 110 comprises an outer member, and an inner member located within the outer member. The suction channel 112 can be located inside the inner member. The irrigation channel 114 can be located outside of the outer member. In some configurations, in addition to or in lieu of supplying irrigation fluid through the irrigation channel 114, the irrigation fluid may be supplied through a gap defined between the inner and outer members of the medical device 110, hereinafter referred to as an "irrigation gap". One of the irrigation channel 114 or the irrigation gap may be selectively activated to supply irrigation fluid to the medical device 110. In some examples, both the irrigation channel 114 and the irrigation gap can be activated to supply irrigation fluid simultaneously. This may advantageously allow a clinician to regulate how much irrigation fluid is used during a procedure. For example, when more tissue debris or stone fragments are produced or when a channel is clogged, both the irrigation channel 114 and the irrigation gap can be activated to provide a larger volume of fluid to the medical device 110.

The control module 160 can be configured to control the operation of the medical device 110, including one or more of tissue resection or stone ablation, illumination, imaging, irrigation, and suction, among other functionalities during an endoscopic procedure. In an example, the control module 160 may be implemented as a part of a microprocessor circuit, such as a dedicated processor, application specific integrated circuit (ASIC), microprocessor, or other type of processor for processing information, generating control signals to activate, deactivate, or change the operation of a component of the system 100. Alternatively, the microprocessor circuit may be a processor that may receive and execute instructions of performing the functions, methods, or techniques described herein.

Figure 3A:
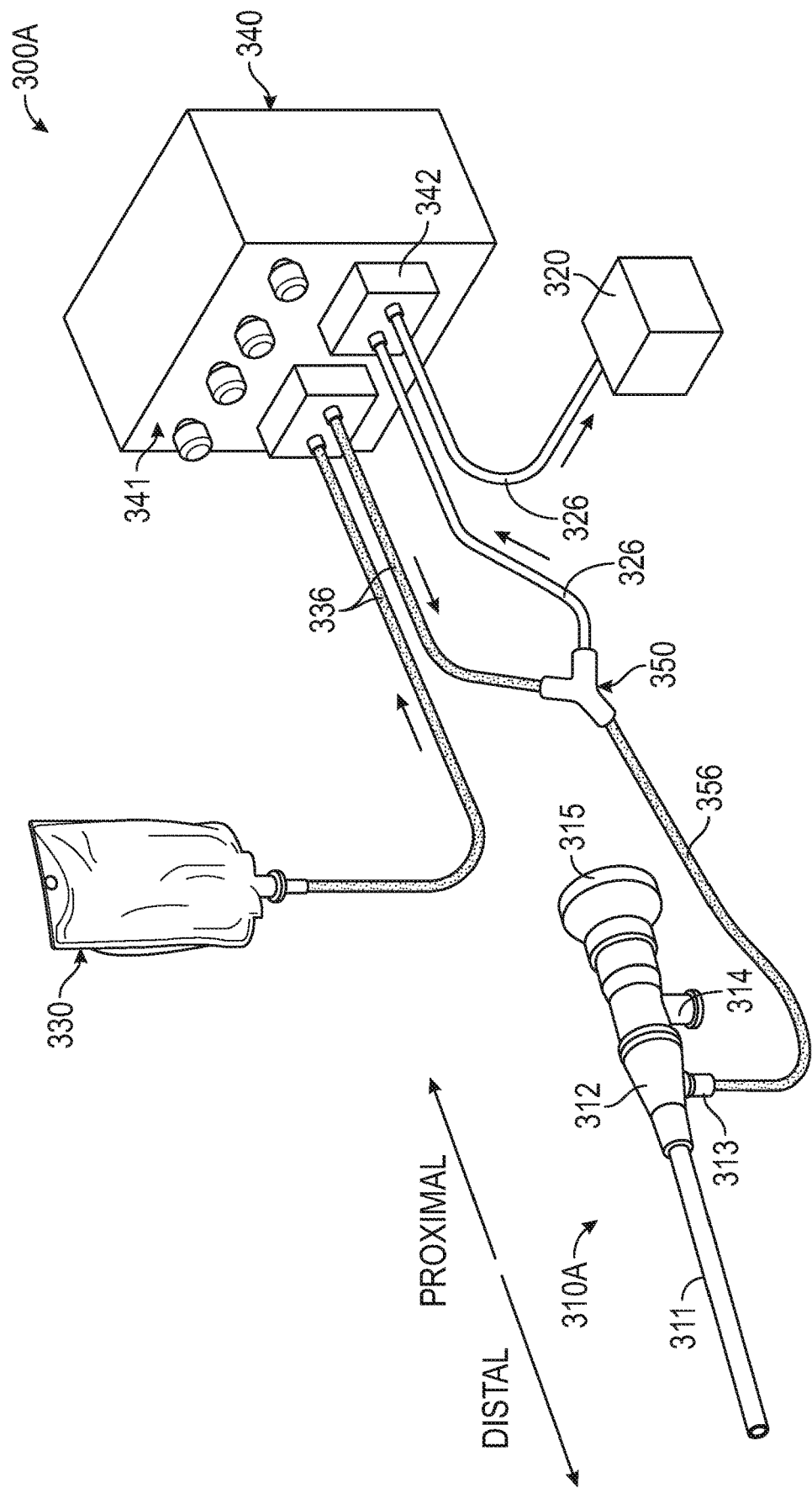
FIGS. 3A-3B are diagrams illustrating endoscope systems that can maintain the in situ pressure of an anatomical environment at substantially a desired level during an endoscopic procedure.
Figure 3B:
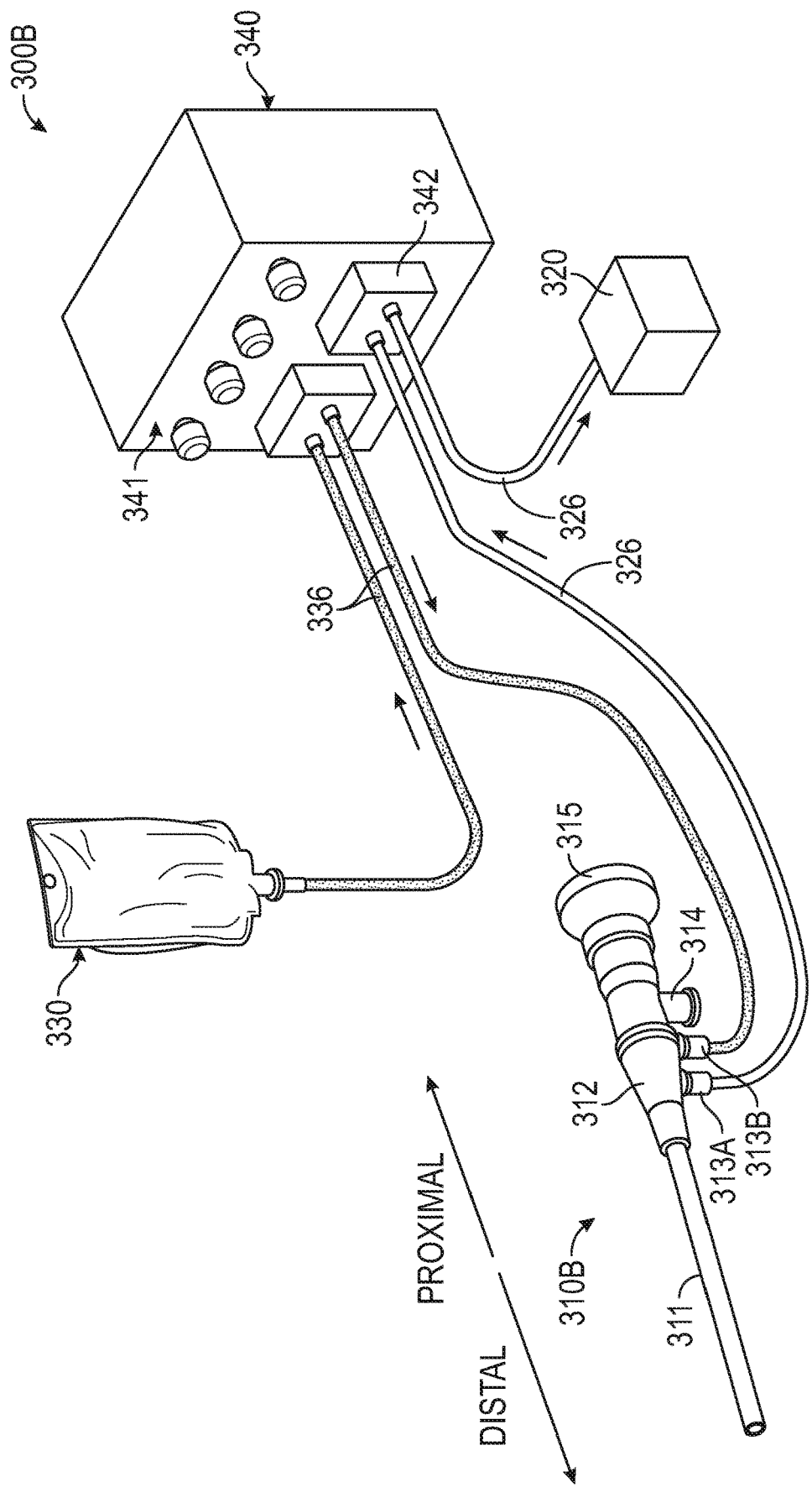

The control module 160 may be at least partially implemented in a unit separate from the medical device 110, such as that illustrated in FIGS. 3A-3B. Alternatively, portions of the control module 160 may be integrated into or otherwise attached to the medical device 110. In some examples, the control module 160 may include circuit sets that, alone or in combination, perform the functions, methods, or techniques described herein. In an example, hardware of the circuit set may include invariably connected components designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 1, the control module 160 can be coupled to a user interface 140, and receive therefrom user commands for activating, deactivating, or adjusting one of more functionalities of the medical device 110. The user interface 140 may be at least partially integrated into or otherwise attached to the medical device 110. Alternatively, the user interface 140 may be separate from the medical device 110, as an exemplary system illustrated in FIGS. 3A-3B. The user interface 140 can be mobile, and can be attached to the medical device 110 and fluid system (e.g., pump, irrigation). In an example, the user interface 140 may include one or more user controls that allow a user (e.g., a clinician) to turn ON or OFF suction, or to adjust suction flow rate or suction pressure. The user controls may be located on the mobile user interface separate from the medical device 110. Alternatively, the user controls may be located on the medical device 110, such as a hand piece of an endoscope or a tissue removal device, such as the device illustrated in FIG. 2A. The control module 160, in response to the user command, can activate or deactivate suction flow from the suction source 120, or to increase or decrease the suction pressure applied to the working channel 111 to achieve the desired suction flow rate. Similarly, the user interface 140 may include one or more user controls that allow the user to turn ON or OFF irrigation, or to adjust irrigation flow rate or irrigation fluid pressure (e.g., via a pump). The control module 160, in response to the user command, can activate or deactivate irrigation flow from the irrigation source 130, or to increase or decrease the irrigation flow rate through working channel 111.

In some examples, the user controls on the user interface 140 can include a depressible flushing control button that, when depressed repeatedly, cycles through one or more irrigation levels and/or suction levels, before turning off the irrigation and suction. In some examples, irrigation and suction can be controlled together with a single control. Other suitable control elements can also be used, such as a positionable slide, a positionable lever, or a positionable dial that can specify an irrigation level and/or a suction level. In some examples, the user interface 140 may allow a user to select from one of a plurality of specified discrete irrigation levels or suction levels, or alternatively specify the irrigation level or the suction level in a continuous (e.g., a non-discrete) manner.

In addition to or in lieu of independent control of suction and irrigation, the control module 160 may automatically control one of the irrigation or suction based on a status of the other of the irrigation or suction. In an example, the control module 160 may turn ON suction automatically when the medical device is powered, or when the irrigation source 130 supplies irrigation fluid to the medical device 110; and turn OFF suction automatically when the medical device is not powered, or when the irrigation source 130 ceases to supply irrigation fluid to the medical device 110. In an example, the control module 160 may automatically adjust the irrigation flow rate or fluid volume (e.g., by activating or deactivating flow in the irrigation gap defined between the inner and outer members) in response to the suction flow rate. For example, at an increased suction (e.g., due to a large amount of unwanted matters to be removed), the control module 160 may automatically increase the irrigation flow rate, or supply irrigation fluid via both the irrigation channel 114 and the irrigation gap. Conversely, at a reduced suction (e.g., due to a small amount of unwanted matters to be removed), the control module 160 may automatically decrease the irrigation flow rate, or supply irrigation fluid via only one, but not both, of the irrigation channel 114 or the irrigation gap.

The control module 160 can include a pressure controller 162 configured to keep the pressure of the anatomical environment (also referred to as the "environmental pressure") under control, such as to maintain the environmental pressure at substantially a desired pressure level (e.g., a predetermined level, or as specified by a user via the user interface 140). In an example, the environmental pressure is deemed to be maintained at the desired pressure level if the difference between the environmental pressure measurement (such as by a pressure sensor) and the desired pressure falls within a range of tolerance, e.g., ±5-10% as a non-limiting example. A desired pressure level to be maintained at the anatomical site of the anatomical environment 101 can be received from the user interface 140. As stated previously, suction may result in a negative pressure change at the anatomical site, while irrigation may result in a positive pressure change at the anatomical site. Negative and positive pressure changes may pose adverse effect on internal organs exposed to the anatomical site. Maintaining the environmental pressure at a controlled pressure level can increase patient safety and effectively reduce procedure time. In some examples, in addition to or in lieu of receiving a desired pressure level, a desired flow condition can be received, such as from the user interface 140. The desired flow condition includes information about inflow (e.g., a flow rate of irrigation fluid applied to the anatomical environment) relative to outflow (e.g., a flow rate of suction applied to the anatomical environment). The desired flow condition corresponds to the desired pressure to be applied to the anatomical environment. For example, a desired flow condition of substantially equal inflow rate and outflow rate corresponds to a substantially net-zero environmental pressure, a desired flow condition of a higher inflow rate than outflow rate corresponds to a positive environmental pressure, and a desired flow condition of a lower inflow rate than outflow rate corresponds to a negative environmental pressure. The pressure controller 162 can control one or more of an irrigation flow rate or a suction flow rate through one or more working channels to maintain the desired flow condition during the procedure.

The pressure controller 162 can achieve the controlled pressure by automatically activating, deactivating, or adjusting one or more of suction or irrigation. The sensor circuit 150 can monitor the pressure of the anatomical environment (the "environmental pressure") during the endoscopic procedure. In an example, the sensor circuit 150 can be coupled to a pressure sensor to sense the environmental pressure, or a signal indicative of or otherwise correlated to the environmental pressure. Examples of the pressure sensor can include resistive, capacitive, piezoelectric, optical, or Micro Electro-Mechanical System (MEMS) pressure sensors. In an example, the pressure sensor may be attached to or integrated into a distal portion of the medical device 110, such as a distal tip of an insertable tubular portion of an endoscope, such that the pressure sensor is in contact with the anatomical environment 101. In an example, the pressure sensor may be positioned at a more proximal location inside the tubular portion of the endoscope away from the anatomical environment 101. The control module 160 can receive from the user interface 140 a desired environmental pressure to be maintained during the procedure. The control module 160 can compare the sensed environmental pressure to the desired environmental pressure, and adjust one or more of an irrigation flow rate or a suction flow rate to drive the environmental pressure towards a level of the desired environmental pressure. An exemplary system for regulating the environmental pressure via automatic adjustment of suction and/or irrigation flow rates is discussed below with reference to FIG. 4.

The user interface 140 may include an output unit, such as a display, to present information collected during the endoscopic procedures including, for example, images (including live video) of the surgical field, operating status of the medical device 110 including status of the working channel 111, information about channel state such as a clogged channel or successful unclogging, and environmental pressure as sensed by the sensor circuit 150, among others.

FIG. 2A illustrates a perspective view of a powered tissue removal device 200, which is an example of the medical device 110. The powered tissue removal device 200 can include a hand piece 210 and a tubular assembly 222 extending from the hand piece 210. The tubular assembly 222 comprises a proximal portion 226 located at the hand piece 210, and an opposing distal portion 228. While the distal portion 228 is illustrated as being a "straight shaft" aligned with the rest of the tubular assembly 222, in some examples, the distal portion 228 may be bent or angled relative to the rest of the tubular assembly 222, including the proximal portion 226.

An exemplary configuration of the distal portion 228 is illustrated in FIG. 29. The tubular assembly 222 comprises an outer tubular member 252 and an inner tubular member 254 that is located inside of the outer tubular member 252. The outer member 252 comprises an outer member window 262. The inner member 254 comprises a cutting portion 264 and a suction channel 274 defined inside the inner member 254. The inner member 254 or the cutting portion 264 comprises an inner member window 266 that is in communication with the suction channel 274.

The powered tissue removal device 200 comprises an irrigation channel 272 located external to, or outside of, the outer member 252. The irrigation channel 272 extends along a length of the outer member 252. A proximal end of the irrigation channel 272 comprises a proximal irrigation port 282 that is in fluid communication with the irrigation source 230, and a distal end of the irrigation channel 272 comprises a distal irrigation port 284 that is attached to the powered tissue removal device 200 or the outer member 252.

The powered tissue removal device 200 can be coupled to an energy source 240, a suction source 220, and an irrigation source 230. The energy source 240 is configured to power the powered tissue removal device 200, the suction source 220, the irrigation source 230, or a combination thereof. The suction source 220, which is an embodiment of the suction source 120, can be in fluid communication with the suction channel 274 defined inside the inner member 254. The suction source 220 is configured to apply suction to, or pull vacuum from, the powered tissue removal device 200 via the suction channel 274. The irrigation source 230, which is an embodiment of the irrigation source 130, can be in fluid communication with the irrigation channel 272 located external to or outside of the outer member 252. The irrigation source 230 can alternatively or additionally be in fluid communication with a gap between the inner member 254 and the outer member 252.

The powered tissue removal device 200 includes one or more user controls 224 for operating the powered tissue removal device 200, the energy source 240, the suction source 220, the irrigation source 230, or a combination thereof. By way of example and not limitation, the user controls 224, which are embodiments of the user interface 140, can be located at the hand piece 210 to allow easy access and manipulation by the user during a procedure. In an example, the user controls 224 may allow a user to manually control the debridement, activate, deactivate, or adjust one or more of an irrigation flow rate or a suction flow, among other irrigation or suction parameters.

The powered tissue removal device 200 includes a control module (not shown) at least partially located inside the hand piece 210. The control module, which can be an embodiment of the control module 160, can be configured to control the operation of the powered tissue removal device 200 in response to user commands from the user controls 224, including one or more of tissue debridement, irrigation, suction, among other functionalities. In an example, the control module may activate and adjust one or more of irrigation flow parameters or one or more suction flow parameters to keep the pressure of the anatomical environment (the "environmental pressure") under control, such as to maintain the environmental pressure at substantially a user-specified desired pressure during the procedure, as discussed above with reference to FIG. 1.

FIGS. 3A-3B illustrate respectively, by way of example, endoscope systems 300A and 300B, for use in an endoscopic procedure. The endoscope systems 300A and 300B are embodiments of the system 100. Referring to FIG. 3A, the system 300A comprises an endoscope 310A, a suction source 320, an irrigation source 330, and a suction/irrigation control unit 340. The endoscope 310A, which is an example of the medical device 110, can extend into a sheath including a tube 311 extending from a distal end to a hub 312. The hub 312 terminates at a proximal end. The endoscope 310 can include a light port 314 and a visual port 315. The light port 314 may function to provide light into the endoscope, and out of the tube 311 of the endoscope, such that a feature of interest in the anatomical environment (e.g., resected tissue, or calculi and mass) is illuminated. The light port is advantageous to enhance visibility, for instance, when the feature of interest is located in low light conditions. The visual port 315 may function to provide a viewing window that allow a user to observe a feature of interest. In an example, the visual port 315 may be an optical window at the proximal end that provides visual access to a viewing lens at the distal end. In another example, the visual portion 315 may provide a connection point to a camera to take images or video of the feature of interest and the anatomical environment. The images or video can be output and displayed on a monitor.

The endoscope 310A can include an irrigation/suction port 313 for receiving suction or irrigation fluid. The irrigation/suction port 313 can be located on an exterior of the hub 312, or other locations on the endoscope 310A such as a proximal end of the endoscope 310A. The irrigation/suction port 313 is open to a working channel (not shown) inside the tube 311. The working channel can be sized, shaped, and configured to transport irrigation fluid and/or for suction. In an example, the same working channel can be used for irrigation and suction (also referred to as a unified irrigation/suction channel). In another example, an irrigation channel and a suction channel are separately disposed within the tube 311.

In an example, the endoscope 310 can be a nephroscope. During use, a flexible distal portion of the tube 311 may be surgically inserted into the kidney of the patient. The proximal portion of the tube 311 can remain outside the body of the patient. Inside the tube 311 can include an optical fiber extending along the length of the endoscope 310. The optical fiber can be a multi-mode fiber or a single-mode fiber. A laser, external to the nephroscope, can generate the laser beam. The laser beam can be coupled into a proximal end of the optical fiber via a suitable connector. The optical fiber can deliver laser beam to the kidney stone to ablate the kidney stone into fragments. In some examples, the laser beam can have a wavelength that corresponds to a spectral peak of absorption of human blood and saline, such as 2100 nm, 1942 nm, and others. In general, delivering laser beam that has significant absorption in blood and saline can be beneficial, because such laser beam can be minimally invasive on surrounding tissue, which can reduce or eliminate damage to the tissue at or near the kidney stone. A laser controller can be located on a graspable proximal portion of the endoscope 310. Similar to the user controls 224 that enables a manual control of the debridement as illustrated in FIG. 2A, the laser controller can allow a user to toggle a state of the laser beam between an operational state ("ON") and a non-operational state ("OFF"). In some examples, a user can adjust one or more settings of the laser, such as the output power, on a housing of the laser, rather than via the laser controller.

The suction/irrigation control unit 340 can provide suction and irrigation to the endoscope 310 during an endoscopic procedure, while keeping the pressure of the anatomical environment under control, such as to maintain the pressure at substantially at a user-specified pressure level (e.g., the user-specified pressure with a tolerance such as ±5-10%). The suction/irrigation control unit 340 can include a pressure monitor (which is an embodiment of the sensor circuit 150), a control module (which is an embodiment of the control module 160), a pump, a power source. The control module can be in communication with a user interface 341 (which is an embodiment of the user interface 140), such as located on an exterior of the suction/irrigation control unit 340, for controlling the control module.

The suction source 320 can be connected to suction/irrigation control unit 340 via an external suction line 326. The suction/irrigation control unit 340 includes a control valve 342 configured to control the suction between the suction source 320 and the endoscope 310 so that suction may be turned off during all or a portion of the application cycle of the irrigation fluid. The irrigation source 330 can be connected to the suction/irrigation control unit 340 via an external irrigation line 336. The pump included in the suction/irrigation control unit 340 can pressurize the irrigation fluid before entering the endoscope 310 via the irrigation line 336. As illustrated in FIG. 3A, the external suction line 326 and the external irrigation line 336 can be connected together at a common fitting 350, which can be coupled to a common line 356 for supplying the fluid or suction to the endoscope 310 via the irrigation/suction port 313.

The control module included in the suction/irrigation control unit 340 may be configured to control the operation of the endoscope 310 in response to user commands from the user interface 341. In an example, the control module may automatically activate and adjust one or more of irrigation flow paramours or one or more suction flow parameters to keep the pressure of the anatomical environment (the "environmental pressure") under control, such as to maintain the environmental pressure at substantially a user-specified pressure level, as discussed above with reference to FIG. 1.

The system 330B as illustrated in the FIG. 3B is similar to the system 330A, and comprises an endoscope 310B, a suction source 320, an irrigation source 330, and a control suction/irrigation control unit 340. Similar to the endoscope 310A, the endoscope 310B can include a tube 311, a hub 312, a light port 314, and a visual port 315. However, instead of a single irrigation/suction port 313, the endoscope 310B includes separate suction port 313A and irrigation port 313B, adapted to be in fluid communication with the suction source 320 and the irrigation source 330, respectively. The suction source 320 is fluidly coupled to the suction port 313A via the external suction line 326. The irrigation source 330 is fluidly coupled to the irrigation port 313B via the external irrigation line 336. The suction port 313A and the irrigation port 313B can each open to one or more working channels inside the tube 311. In an example, an irrigation channel and a suction channel are separately disposed within the tube 311. The suction port 313A can be selectively open to the suction channel or the irrigation channel. Similarly, the irrigation port 3139 can be selectively open to the suction channel or the irrigation channel inside the tube 311.

Figure 4:
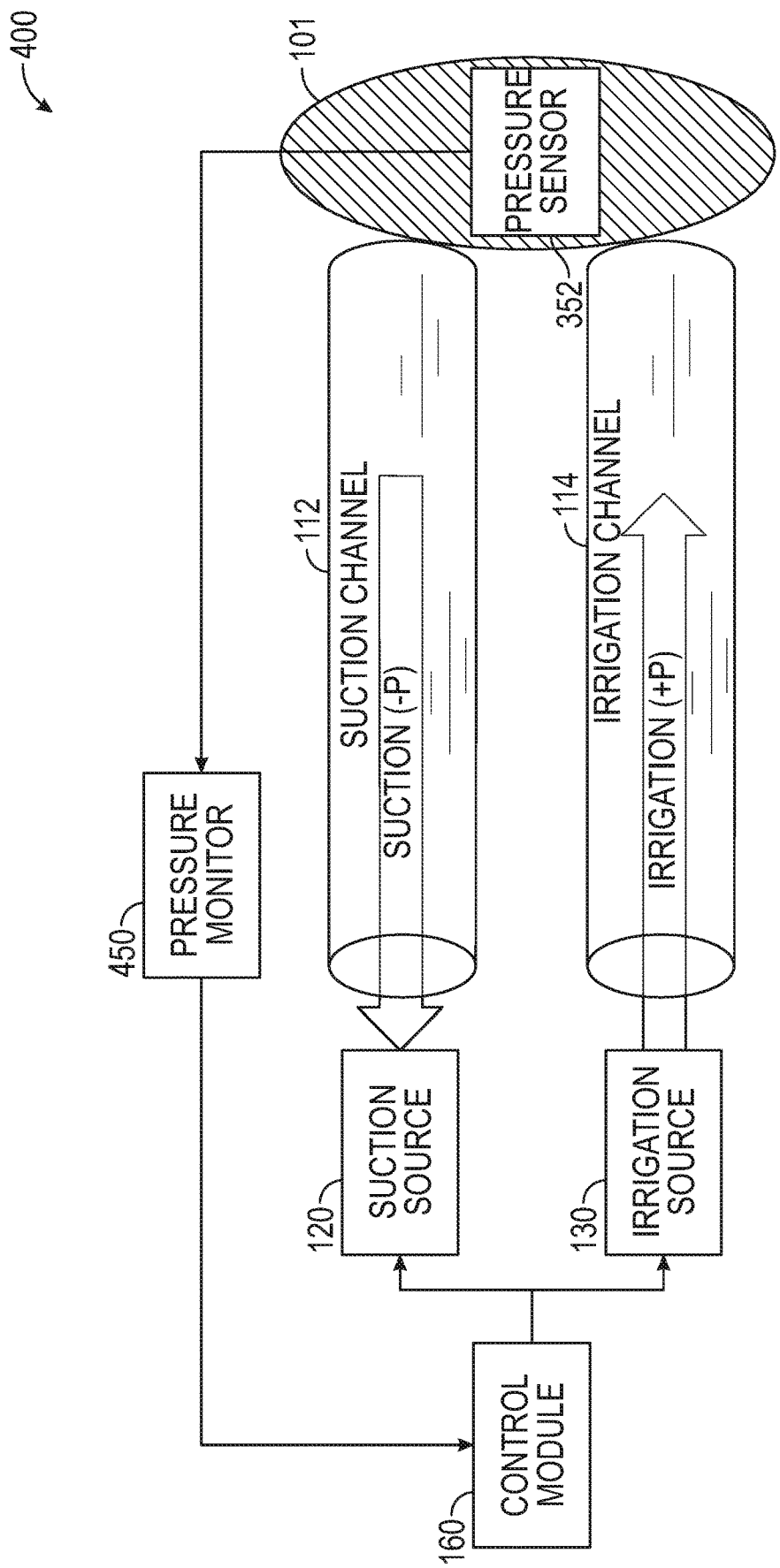
FIG. 4 is a diagram illustrating an exemplary feedback-controlled pressure regulation system.

FIG. 4 is a diagram illustrating an exemplary feedback-controlled pressure regulation system 400, which is an embodiment of the environmental pressure control portion of the system 100. The system 400 can be configured to regulate the environmental pressure at the anatomical site via automatic adjustment of suction and/or irrigation flow rates in the respective suction channel 112 and irrigation channel 114. In an example, a longitudinal axis of the suction channel 112 and a longitudinal axis of the irrigation channel 114 may be parallel to each other. In an example, the suction channel 112 and the irrigation channel 114 may be coaxially disposed with a common axis, such as in a nested configuration. In an example, irrigation and suction can be applied through the same working channel, such as a unified irrigation/suction channel, at different times. A pressure monitor 450 can monitor the pressure of the anatomical environment 101 via a pressure sensor 352. By way of example and not limitation, the control module 160 may include a Proportional-Integral (PI) controller, or a Proportional-Integral-Derivative (PID) controller, among other feedback controllers. The difference between the sensed pressure (at the pressure monitor 450) and the desired pressure, also referred as the "error", can be used to determine the P, I, or D terms in the feedback controller.

Depending on the desired pressure (or the desired flow condition) provided by a user, the system 500 may operate in a stable pressure mode when the desired pressure is substantially net-zero (corresponding to a desired flow condition of substantially equal inflow rate of irrigation fluid applied to the anatomical environment and outflow rate of suction applied to the anatomical environment), or a pressure control mode when the desired pressure is a positive pressure or a negative pressure (corresponding to a desired flow condition of an imbalance between the inflow rate and the outflow rate). When operating in the stable pressure mode, the irrigation flow rate or the suction flow rate can be manually adjusted by a user, such as via respective user controls on the user interface 140. During an endoscopic procedure, an increase in the irrigation flow rate may result in an increase in the environmental pressure at the anatomical site, which can be sensed by the pressure monitor 450. The control module 160 can responsively activate suction by applying suction pressure to the suction channel 112. Suction can produce a negative pressure to offset the increased pressure produced by the irrigation. The control module 160 can adjust the suction flow rate or the suction pressure until the pressure increase (due to the increased irrigation) is substantially neutralized by the suction flow. The environmental pressure can then be driven towards, and maintained at, substantially zero.

Likewise, an increase in the suction flow rate may result in a decrease in the environmental pressure at the anatomical site. The control module 160 can responsively activate irrigation by providing a flow of irrigation fluid to the irrigation channel 114. Irrigation can produce a positive pressure to offset the decreased pressure produced by the suction. The control module 160 can adjust the irrigation flow rate until the pressure drop (due to the increased suction) is substantially neutralized by the irrigation flow. The environment pressure can then be driven towards, and maintained at, substantially zero.

In certain circumstances, it is desirable to maintain a positive or a negative environmental pressure, at the anatomical site. A controlled positive pressure within a safety range can help distend an anatomy (e.g., ureters, kidney, uterus, or other organs) during the endoscopic procedure to allow for better visibility of the anatomy via the scope, without causing tissue damage due to excessive positive pressure. A positive pressure may also prevent tissue debris or stone fragments from getting stuck in the anatomy and assist in the removal of them from the anatomy. In some cases, maintaining a controlled negative pressure within a safety range during the endoscopic procedure can also facilitate debris extraction from the anatomy, without putting an internal organ at a risk of excessive negative pressure.

When a positive desired environmental pressure is provided by a user such as via the user interface 140, the system 400 may operate in a pressure control mode. The control module 160 can automatically increase the irrigation flow rate through the irrigation channel 114 to increase the positive environmental pressure at the anatomical site. Additionally or alternatively, the control module 160 can automatically decrease the suction flow rate through the suction channel 112 to reduce the negative pressure at the anatomical site. The automatic adjustments of irrigation and/or suction can be continued until the sensed environmental pressure reaches substantially a level of the desired positive pressure.

Likewise, the system 400 may operate in the pressure control mode when a negative desired environmental pressure is provided by the user such as via the user interface 140. The control module 160 can automatically increase the suction flow rate through the suction channel 112 to increase the negative environmental pressure at the anatomical site. Additionally or alternatively, the control module 160 can automatically decrease the irrigation flow rate through the irrigation channel 114 to reduce the positive pressure at the anatomical site. The automatic adjustments of irrigation and/or suction can be continued until the sensed environmental pressure reaches substantially a level of the desired negative pressure.

The control module 160 can include a safety mechanism to keep the pressure of the anatomical environment within a safety range defined by a lower bound of negative pressure and an upper bound of positive pressure. If the sensed environmental pressure reaches the upper bound of positive pressure, the control module 160 can automatically shut down, reduce, or maintain at present rate of irrigation flow to prevent further increase in the environmental pressure. Likewise, if the sensed environmental pressure reaches the lower bound of negative pressure, the control module 160 can automatically shut down, reduce, or maintain at present rate of suction flow to prevent further decrease in the environmental pressure. When the system operates in the pressure control mode, the desired positive pressure and the desired negative pressure received from a user are checked to ensure that they fall within the safety range. In a non-limiting example, the desired positive pressure is 5 pound-force per square inch (psi) (or approximately 34.5 kilopascal (kPa)), the desired negative pressure is −5 psi (or approximately −34.5 kPa), and the safety range is between a lower bound of −6 psi (or approximately 41.4 kPa) and an upper bound of 6 psi (or approximately 41.4 kPa). In an example, a warning can be issued (e.g., from the user interface 140) if the desired positive pressure received from a user exceeds the upper bound of positive pressure, or if desired negative pressure is lower than the safety bound of negative pressure. With such a safety mechanism, the control module 160 can maintain the environmental pressure at a user-specified level, while at the same time preventing or minimizing excess positive or negative pressures imposed on the anatomical environment during the procedure.

Figure 5:
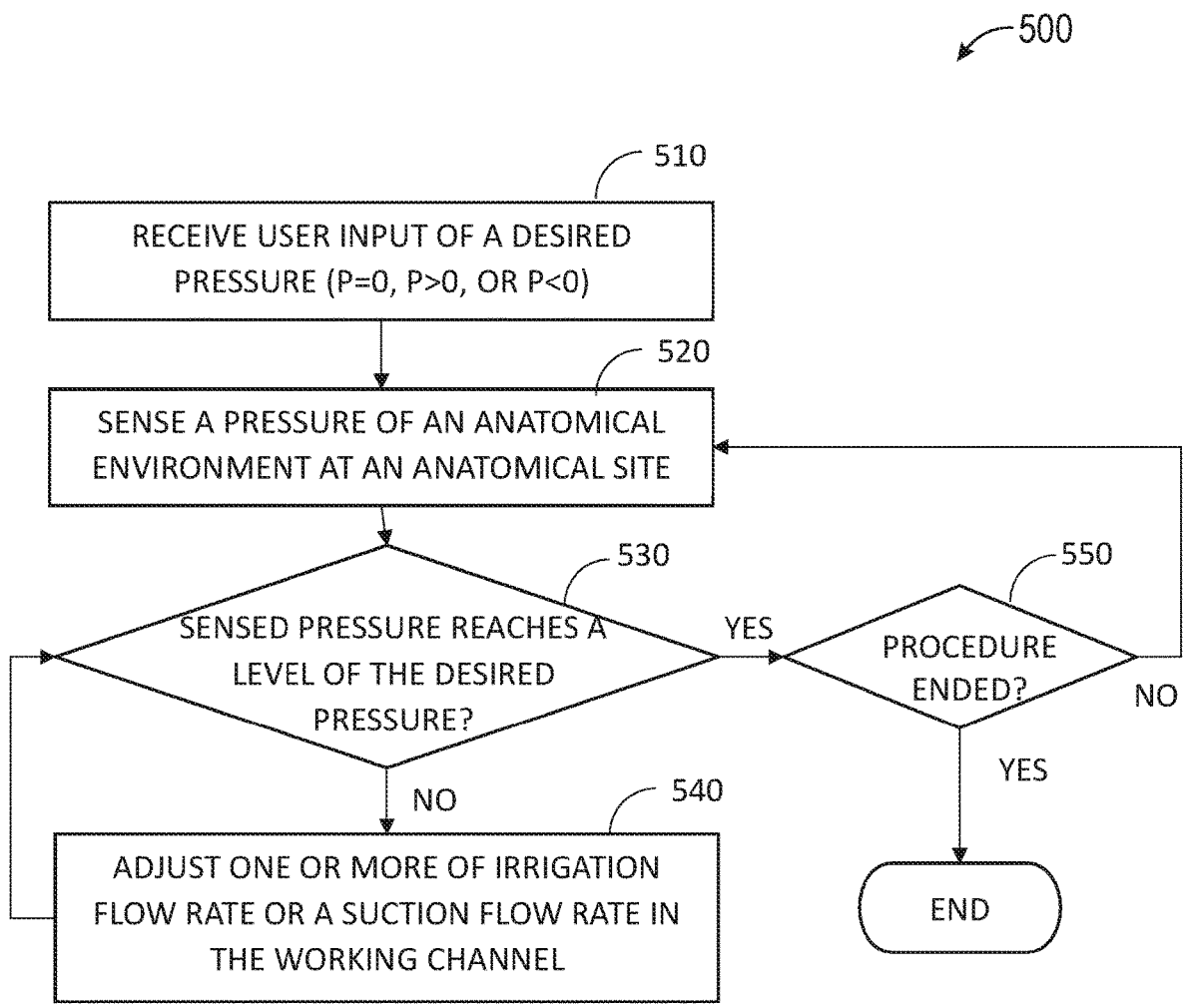
FIG. 5 is a flow chart illustrating a method of maintaining a pressure of an anatomical environment at an anatomical site during a minimally invasive procedure.

FIG. 5 is a flow chart illustrating a method 500 for maintaining a pressure of an anatomical environment at an anatomical site (the "environmental pressure") in a patient during a minimally invasive procedure, such as an endoscopic procedure. Examples of the medical device can include a tissue removal device such as illustrated in FIG. 2, or an endoscope such as illustrated in FIGS. 3A-3B, among others. The medical device can include a tubular portion insertable into the interior of a hollow organ or a cavity of the body to assist in medical diagnosis or surgical treatment. The medical device can comprise one or more working channels configured to provide irrigation fluid to the anatomical site, and to transport the tissue debris, calculi and mass, body fluid, and irrigation fluid, referred to herein collectively as "unwanted matters", away from the anatomical site. The working channel can be at least partially located inside the tubular portion of the medical device. In an example, the working channel is a unified irrigation/suction channel controllably used for irrigation and suction (e.g., at different times). In another example, the working channels can include separate irrigation channel and suction channel disposed within the tubular portion of the medical device. The irrigation channel and the suction channel may each receive irrigation fluid or suction pressure, such as under automatic control by a controller unit to perform different tasks or to fulfill different functions during an endoscopic procedure in accordance with various embodiments discussed in this document.

The method 500 comprises one or more processes of operating an unclogging system, such as the system 100 or variant thereof, such as one of the systems 200, 300A, or 300B. Although the processes of the method 500 are drawn in one flow chart, they are not required to be performed in a particular order. In various examples, some of the processes can be performed in a different order than that illustrated herein.

The method 500 can regulate the environmental pressure by automatically activating, deactivating, or adjusting one or more of suction or irrigation flow rates in one or more working channels. As stated previously, suction may result in a negative pressure change at the anatomical site, while irrigation may result in a positive pressure change at the anatomical site. Negative and positive pressure changes may pose adverse effect on internal organs exposed to the anatomical site. Maintaining the environmental pressure at a controlled pressure level can increase patient safety and effectively reduce procedure time.

At 510, a desired environmental pressure can be received from a user, such as via the user interface 140. The desired pressure represents a pressure to be maintained at the anatomical environment during the procedure. In various examples, the desired pressure can be one of a substantially net-zero pressure, a desired positive pressure, or a desired negative pressure.

In some examples, in addition to or in lieu of receiving a desired pressure, a desired flow condition can be received at 510, such as from the user interface 140. The desired flow condition includes information about inflow (e.g., a flow rate of irrigation fluid applied to the anatomical environment) relative to outflow (e.g., a flow rate of suction applied to the anatomical environment), and corresponds to the desired pressure to be applied to the anatomical environment. One or more of an irrigation flow rate or a suction flow rate through one or more working channels can be varied to maintain the desired flow condition during the procedure.

At 520, pressure of the anatomical environment (the "environmental pressure") can be sensed, such as using a pressure sensor. The pressure sensor may be attached to or integrated into a distal portion of the medical device, such that the sensor is in contact with the anatomical environment. Examples of the pressure sensor can include resistive, capacitive, piezoelectric, optical, or Micro Electro-Mechanical System (MEMS) pressure sensors.

At 530, the sensed tissue present can be compared to the desired pressure. If the sensed pressure does not reach substantially a level of the desired pressure, then at 540 one or more of an irrigation flow rate or a suction flow rate through the working channel can be adjusted, such as using the pressure controller 162, to drive the environmental pressure towards a level of the desired pressure. As described above with reference to FIG. 4, suction applied to the suction channel can produce a negative pressure of the anatomical environment, which can offset the increase in environmental pressure produced by an increased irrigation flow rate. Similarly, a flow of irrigation fluid provided to the irrigation channel can produce a positive pressure of the anatomical environment, which can offset a decrease in environmental pressure produced by suction. The suction flow rate or the suction pressure, and irrigation flow rate or irrigation pressure can be adjusted, such as via the pressure controller 162, to maintain the environmental pressure at substantially a level of the desired pressure. Exemplary methods of adjusting the suction and/or irrigation to maintain a desired environmental pressure, such as a net-zero pressure, a desired positive pressure, or a desired negative pressure are discussed below with references to FIGS. 6A-6B and 7A-7B.

If at 530 the sensed environmental pressure reaches and maintains at substantially a level of the desired pressure (that is, within a range of tolerance, such as ±5-10% of the desired pressure), then at 550 the procedure is checked for completion. If the procedure is not completed, then the pressure sensing at 520 and irrigation/suction flow adjustments at 540 can be continued until the completion of the procedure.

FIGS. 6A-6B are flow charts illustrating respective methods 600A and 600B of maintaining a balanced environmental pressure (e.g., substantially a net-zero pressure) of the anatomical environment at an anatomical site during an endoscopic procedure, or maintaining a desired flow condition of substantially equal inflow rate of irrigation fluid applied to the anatomical environment and outflow rate of suction applied to the anatomical environment. The equal inflow and outflow corresponds to substantially net-zero pressure of the anatomical environment. The balanced environment pressure, or the equal inflow and outflow rates in a working channel, can be achieved by automatically activating, deactivating, or adjusting one or more of suction or irrigation flow rates in one or more working channels. Maintaining a substantially net-zero environmental pressure is also referred to as a stable pressure mode. The methods 600A and 600B can be implemented in and executed by a pressure controller, such as the pressure controller 162. The processes in any of these methods are not required to be performed in a particular order. For example, some steps can be performed in a different order than that illustrated herein.

The method 600A includes steps of automatic activation and controlled application of suction pressure in response to an increased irrigation through to a working channel during an endoscopic procedure. At 611, a user command of increasing an irrigation flow rate can be received from a user interface. The irrigation flow can produce a positive pressure change at the anatomical environment, which can be sensed at 612 using a pressure sensor. In response to the sensed positive pressure change, at 613, suction can be activated, such as by fluidly coupling a suction source to the working channel under the control of the pressure controller 162. The pressure controller 162 can include a Proportional-Integral (PI) controller, or a Proportional-Integral-Derivative (PID) controller, among other feedback controllers. The difference between the sensed pressure and the desired pressure, also referred to as the "error" terms, can be used to determine the P, I, and D terms in the feedback controller. In some examples, the irrigation at 611 and suction at 613 can be applied to separated channels, such as an irrigation channel and a suction channel as illustrated in FIG. 4. Alternatively, irrigation at 611 and suction at 613 can be applied to the same working channel (the "unified suction/irrigation channel") such as at different times.

The suction through the working channel at 613 can produce a negative pressure change, which can offset the increased pressure produced by the irrigation at an increased flow rate at 611. To achieve the desired environmental pressure, the suction flow rate, or the suction pressure, can be adjusted based on the environmental pressure measurement. At 614, the sensed tissue present is checked against the desired net-zero pressure. If the sensed pressure does not reach substantially a level of the desired pressure, then the suction flow rate can be further adjusted at 613 until the increase in the sensed pressure (resulted from the increased irrigation) is substantially neutralized by the suction flow, such that the environmental pressure can be driven towards, and maintained at, substantially zero.

The method 600B includes steps of automatic activation and controlled application of a flow of irrigation fluid in response to suction applied to a working channel during an endoscopic procedure. At 621, a user command of applying suction to a working channel can be received from a user interface. The application of suction pressure can produce a negative pressure change at the anatomical environment, which can be sensed by a pressure sensor at 622. In response to the sensed negative pressure change, at 623, irrigation can be activated to provide irrigation flow into the working channel. As illustrated in FIG. 4, the suction at 621 and the irrigation at 623 can be applied to separate channels, such as an irrigation channel and a suction channel. Alternatively, irrigation and suction can be applied to a unified suction/irrigation channel such as at different times.

The irrigation through the working channel at 623 can produce a positive pressure change, which can offset the decrease in pressure produced by the suction at 611. To achieve the desired environmental pressure, the irrigation flow rate, or the irrigation pressure (such as controlled by a pump to pressurize the irrigation fluid before being introduced to the working channel), can be adjusted based on the environmental pressure measurement. At 624, the sensed tissue present is compared to the desired net-zero pressure. If the sensed pressure does not reach substantially a level of the desired pressure, then the irrigation can be further adjusted at 623 until the decrease in the sensed pressure (resulted from the suction applied) is substantially neutralized by the irrigation flow, such that the environmental pressure can be driven towards, and maintained at, substantially zero.

FIGS. 7A-7B are flow charts illustrating respective methods 700A and 700B of maintaining a desired positive or negative pressure of the anatomical environment during an endoscopic procedure, or maintaining a flow condition characterized by a desired imbalance between the inflow rate of irrigation fluid applied to the anatomical environment and outflow rate of suction applied to the anatomical environment. The desired imbalanced flow corresponds to the desired positive or negative pressure of the anatomical environment. The desired pressure condition or the desired flow condition can be achieved by automatically activating, deactivating, or adjusting one or more of suction or irrigation flow rates in one or more working channels. Maintaining the environmental pressure at a controlled positive or negative level is also referred to as a pressure control mode.

The methods 700A and 700B can be implemented in and executed by a pressure controller, such as the pressure controller 162 of the control module. The processes in any of these methods are not required to be performed in a particular order. For example, some steps can be performed in a different order than that illustrated herein.

Referring to FIG. 7A, the method 700A includes steps of automatic activation and controlled application of suction or irrigation to a working channel during an endoscopic procedure to maintain a desired positive pressure of the anatomical environment at the anatomical site. Maintaining a controlled positive pressure within a safety range can help distend an anatomy (e.g., ureters, kidney, or other organs) during the endoscopic procedure to allow for better visibility of the anatomy via the scope, without causing tissue damage due to excessive positive pressure. A positive pressure may also prevent tissue debris or stone fragments from getting stuck in the anatomy, and assist in the removal of these unwanted matters from the anatomy. At 711, a desired positive pressure can be received from a user via a user interface. By way of example and not limitation, the desired positive pressure is 5 psi (approximately 34.5 kPa). At 712, irrigation at an increased flow rate, or suction at a decreased flow rate, can be applied to the working channel. This may result in a positive change in the pressure at the anatomical environment, which can be sensed by a pressure sensor at 713. At 714, the sensed pressure can be compared to the desired positive pressure. If the sensed tissue present does not reach and maintain at the desired positive pressure, then the adjustment of irrigation and/or suction may be continued at 712. This may include, for example, further increasing the irrigation flow rate and/or decreasing the suction flow rate if the sensed pressure is below the desired positive pressure (e.g., the sensed pressure is 4 psi versus a desired positive pressure of 5 psi); or reducing the irrigation flow rate and/or increasing the suction flow rate if the sensed pressure exceeds the desired positive pressure (e.g., the sensed pressure is 6 psi versus a desired positive pressure of 5 psi).

Referring to FIG. 7B, the method 700B includes steps of automatic activation and controlled application of suction or irrigation to a working channel during an endoscopic procedure to maintain a desired negative pressure of the anatomical environment at the anatomical site. Maintaining a controlled negative pressure within a safety range during the endoscopic procedure can also facilitate debris extraction from the anatomy, without putting an internal organ at a risk of excessive negative pressure. At 721, a desired negative pressure can be received from a user from a user interface. An example of the desired negative pressure is −5 psi (approximately −34.5 kPa). At 722, suction at an increased flow rate, or irrigation at a decreased flow rate, can be applied to the working channel. This may result in a negative pressure change at the anatomical environment, which can be sensed by a pressure sensor at 723. At 724, the sensed pressure can be compared to the desired negative pressure. If the sensed tissue present does not reach and maintain at the desired negative pressure, then the adjustment of irrigation and/or suction may be continued at 722. This may include, for example, further increasing the suction flow rate and/or decreasing the irrigation flow rate if the sensed pressure exceeds the desired positive pressure (e.g., the sensed pressure is −4 psi compared to a desired positive pressure of −5 psi); or reducing the suction flow rate and/or increasing the irrigation flow rate if the sensed pressure falls below the desired positive pressure (e.g., the sensed pressure is −6 psi compared to a desired positive pressure of −5 psi).

The methods of controlling the application of irrigation and/or suction through one or more working channels as described above (e.g., methods 500, 600A-600B, and 700A-700B) can effectively avoid or minimize excess positive or negative pressures imposed on the internal organ during an endoscopic procedure. Consequently, overall procedure time can be reduced and patient safety can be improved.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for regulating a pressure at an anatomical site in a patient during a procedure, the system comprising:
    a user input configured to receive from a user a desired pressure, within a safety pressure range between a negative boundary pressure and a positive boundary pressure, to be applied to the anatomical site during the procedure;
    a pressure sensor configured to sense a pressure of the anatomical site;
    a surgical device configured to surgically remove an object from the anatomical site; and
    a control module configured to:
        perform a safety check of the sensed pressure against the safety pressure range; and
        in response to the safety check indicating the sensed pressure falling within the safety pressure range, control one or more of a suction source or an irrigation source fluidly coupled to at least one working channel so as to control one or more of an irrigation flow rate or a suction flow rate through the at least one working channel to exert, respectively, irrigation force or suction force directly to the anatomical site, thereby regulating the pressure of the anatomical site such that the sensed pressure of the anatomical site is maintained at substantially a level of the desired pressure during the procedure,
    wherein the desired pressure represents a pressure that (i) avoids pressure-induced tissue damage during the surgical removal of the object during the procedure, and (ii) facilitates passage of the surgically removed object away from the anatomical site through the at least one working channel.

2. The system of claim 1, wherein:
    the user input is configured to receive a desired flow condition in the at least one working channel, the desired flow condition corresponding to the desired pressure to be applied to the anatomical site; and the control module is configured to control one or more of the irrigation flow rate or the suction flow rate through the at least one working channel to regulate the desired flow condition.

3. The system of claim 1, wherein the control module is configured to:
control the irrigation source fluidly coupled to the at least one working channel to provide an irrigation fluid thereto at an adjustable irrigation flow rate; and
control the suction source fluidly coupled to the at least one working channel to supply a suction pressure thereto at an adjustable suction flow rate.

4. The system of claim 3, wherein the at least one working channel includes an irrigation channel and a suction channel, and
wherein the control module is configured to provide the irrigation fluid to the irrigation channel at the adjustable irrigation flow rate, and to provide the suction pressure to the suction channel at the adjustable suction flow rate.

5. The system of claim 1, wherein the user input is configured to receive a user command of increasing or decreasing one or more of the irrigation flow rate or the suction flow rate.

6. The system of claim 1, wherein the desired pressure is a substantially net-zero pressure of the anatomical site, and wherein the control module is configured to:
in response to an increase in the sensed pressure produced by an increase in the irrigation flow rate, increase the suction flow rate through the at least one working channel to substantially neutralize the increase in the sensed pressure; and
in response to a decrease in the sensed pressure produced by an increase in the suction flow rate, increase the irrigation flow rate through the at least one working channel to substantially neutralize the decrease in the sensed pressure.

7. The system of claim 1, wherein the desired pressure is a positive pressure of the anatomical site, and
wherein the control module is configured to increase the irrigation flow rate or to decrease the suction flow rate through the at least one working channel until the sensed pressure reaches substantially a level of the desired positive pressure.

8. The system of claim 1, wherein the desired pressure is a negative pressure of the anatomical site, and
wherein the control module is configured to decrease the irrigation flow rate or to increase the suction flow rate through the at least one working channel until the sensed pressure reaches substantially a level of the desired negative pressure.

9. The system of claim 1, wherein the surgical device includes a tissue removal device at least partially insertable into the anatomical site, the tissue removal device configured to illuminate at least a portion of the anatomical site and surrounding environment, provide an image of the anatomical site, resect unwanted tissue from the anatomical site, and remove the resected tissue through the at least one working channel, and
wherein the control module is configured to adjust one or more of the irrigation flow rate or the suction flow rate to regulate the pressure of the anatomical site at substantially a level of the desired pressure.

10. The system of claim 1, wherein the surgical device includes a nephroscope at least partially insertable into a portion of a urinary tract of the patient, the nephroscope configured to illuminate renal mass and surrounding environment, provide an image of the illuminated renal mass, break the renal mass into fragments, and remove the renal mass fragments through the at least one working channel; and
wherein the control module is configured to adjust one or more of the irrigation flow rate or the suction flow rate to maintain the pressure of the environment surrounding the renal mass at substantially a level of the desired pressure.

11. The system of claim 1, wherein the control module is configured to, in response to an initiation of surgical removal of the object from the anatomical site, adjust one or more of the irrigation flow rate or the suction flow rate to maintain the pressure of the anatomical site at substantially a level of the desired pressure.

12. The system of claim 1, wherein the control module is further configured to regulate one or more of the irrigation flow rate or the suction flow rate through the at least one working channel in response to the safety check indicating that the sensed pressure is outside the safety pressure range.

13. A method of regulating a pressure applied to an anatomical site in a patient during a procedure, the method comprising:
receiving, via a user input, a desired pressure, within a safety pressure range between a negative boundary pressure and a positive boundary pressure, to be applied to the anatomical site;
sensing a pressure of the anatomical site via a pressure sensor;
surgically removing an object from the anatomical site using a surgical device;
performing a safety check of the sensed pressure against the safety pressure range; and
in response to the sensed pressure falling within the safety pressure range, adjusting one or more of an irrigation flow rate or a suction flow rate through at least one working channel via a control module that controls one or more of a suction source or an irrigation source fluidly coupled to the at least one working channel to exert, respectively, irrigation force or suction force at the anatomical site, thereby regulating the pressure of the anatomical site such that the sensed pressure of the anatomical site is maintained at substantially a level of the desired pressure during the procedure, the desired pressure representing a pressure that (i) avoids pressure-induced tissue damage during the surgical removal of the object during the procedure, and (ii) facilitates passage of the surgically removed object away from the anatomical site through the at least one working channel.

14. The method of claim 13, comprising:
receiving a desired flow condition in the at least one working channel, the desired flow condition corresponding to the desired pressure to be applied to the anatomical site; and
adjusting one or more of the irrigation flow rate or the suction flow rate through the at least one working channel to regulate the desired flow condition.

15. The method of claim 13, wherein the at least one working channel includes an irrigation channel and a suction channel, the method comprising:
controlling the irrigation source to provide an irrigation fluid at an adjustable irrigation flow rate in the irrigation channel; and
controlling the suction source to provide a suction pressure at an adjustable suction flow rate through the suction channel.

16. The method of claim 15, comprising receiving from the user input a user command of increasing or decreasing one or more of the irrigation flow rate or the suction flow rate.

17. The method of claim 13, wherein the desired pressure is a substantially net-zero pressure of the anatomical site, and wherein adjusting the one or more of the irrigation flow rate or the suction flow rate includes:
   in response to an increase in the sensed pressure produced by an increase in the irrigation flow rate, increasing the suction flow rate through the at least one working channel to substantially neutralize the increase in the sensed pressure; and
   in response to a decrease in the sensed pressure produced by an increase in the suction flow rate, increasing the irrigation flow rate through the at least one working channel to substantially neutralize the decrease in the sensed pressure.

18. The method of claim 13, wherein the desired pressure is a positive pressure of the anatomical site, and wherein adjusting the one or more of the irrigation flow rate or the suction flow rate includes increasing the irrigation flow rate or decreasing the suction flow rate through the at least one working channel until the sensed pressure reaches substantially a level of the desired positive pressure.

19. The method of claim 13, wherein the desired pressure is a negative pressure of the anatomical site, and wherein adjusting the one or more of the irrigation flow rate or the suction flow rate includes decreasing the irrigation flow rate or increasing the suction flow rate through the at least one working channel until the sensed pressure reaches substantially a level of the desired negative pressure.

20. The method of claim 13, wherein adjusting one or more of the irrigation flow rate or the suction flow rate is in response to an initiation of surgically removing the object from the anatomical site to maintain the pressure of the anatomical site at substantially a level of the desired pressure.

* * * * *